United States Patent
Baurley et al.

(10) Patent No.: US 11,610,144 B2
(45) Date of Patent: Mar. 21, 2023

(54) BIOSIGNATURE DISCOVERY FOR SUBSTANCE USE DISORDER USING STATISTICAL LEARNING

(71) Applicant: BioRealm LLC, Walnut, CA (US)

(72) Inventors: James W. Baurley, Los Angeles, CA (US); Christopher S. McMahan, Clemson, SC (US); Andrew W. Bergen, Cabin John, MD (US)

(73) Assignee: BIOREALM LLC, Walnut, CA (US)

( * ) Notice: Subject to any disclaimer, the term of this patent is extended or adjusted under 35 U.S.C. 154(b) by 1021 days.

(21) Appl. No.: 16/267,360

(22) Filed: Feb. 4, 2019

(65) Prior Publication Data
US 2019/0244124 A1  Aug. 8, 2019

Related U.S. Application Data

(60) Provisional application No. 62/625,717, filed on Feb. 2, 2018.

(51) Int. Cl.
G06N 20/00 (2019.01)
G06N 7/00 (2023.01)
G16B 40/20 (2019.01)
G06F 17/18 (2006.01)

(52) U.S. Cl.
CPC ............ *G06N 7/00* (2013.01); *G06F 17/18* (2013.01); *G06N 20/00* (2019.01); *G16B 40/20* (2019.02)

(58) Field of Classification Search
None
See application file for complete search history.

(56) References Cited

FOREIGN PATENT DOCUMENTS

EP  2801625 A1 * 11/2014 ......... A61K 31/4178

OTHER PUBLICATIONS

R. Boscolo-Berto, et al., Ethyl glucuronide concentration in hair for detecting heavy drinking and/or abstinence: a meta-analysis, Int. J. Legal Ivied. 127 (3) (2013) 611-619.
E. J. Cone et al., Nonsmoker exposure to secondhand cannabis smoke. III. oral fluid and blood drug concentrations and corresponding subjective effects, J. Anal. Toxicol. 39 (7) (2015) 497-509.
N. L. Benowitz et al., 3rd, Urine cotinine screening detects nearly ubiquitous tobacco smoke exposure in urban adolescents, Nicotine Tob. Res. 19 (9) (2017) 1048-1054.
N. D. Volkow et al., Biomarkers in substance use disorders, ACS Chem. Neurosci. 6 (4) (2015) 522-525. doi:10.1021/ acschemneuro. 5b00067.
H. Yi, P. Breheny et al., Penalized multimarker vs. single-marker regression methods for genome-wide association studies of quantitative traits, Genetics 199 (1) (2015) 205-222.
R. Whelan et al., IMAGEN Consortium, Neuropsychosocial profiles of current and future adolescent alcohol misusers, Nature 512 (7513) (2014), 185-189.

(Continued)

*Primary Examiner* — David R Vincent
(74) *Attorney, Agent, or Firm* — Cislo & Thomas, LLP

(57) ABSTRACT

A method for biomarker discovery for substance use disorders wherein high dimensional data containing a plurality of variables based on a sample size and a number of variables exceeding that sample size are applied to an ensemble of statistical learning models whereby biomarkers of a substance use disorder are identified.

16 Claims, 8 Drawing Sheets

(56) References Cited

OTHER PUBLICATIONS

M. Mamdani et al., Integrating mRNA and miRNA weighted gene Co-Expression networks with eQTLs in the nucleus accumbens of subjects with alcohol dependence, PLoS One 10 {9} (2015) e0137671.
E. R. Gamazon et al., A gene-based association method for mapping traits using reference transcriptome data, Nat. Genet. 47 (9) (2015) 1091-1098.
J. Lonsdale et al.,The Genotype-Tissue expression (GTEx) project, Nat. Genet. 45(6) (2013) 580-585. doi:10 .1038/ng. 2653.
A. Gusev et al., Integrative approaches for large-scale transcriptome-wide association studies, Nat. Genet. 48 (3) (2016), 245-252.
N. Mancuso et al., Integrating gene expression with summary association statistics to identify genes associated with 30 complex traits, Am. J. Hum. Genet. 100 (3) (2017), 473-487.
G. E. Swan et al., Genetic and enviromnental influences on the ratio of 3'hydroxycotinine to cotinine in plasma and urine, Pharmacogenet. Genomics 19 (5) (2009), 388-398. doi:10.1097/FPC.Ob013e32832a404f.
A. Loukola et al., A Genome-Wide association study of a biomarker of nicotine metabolism, PLoS Genet. 11 (9) {2015) e1005498.
N. L. Benowitz et al., Nicotine chemistry, metabolism, kinetics and biomarkers, Handb. Exp. Pharmacol. (192) (2009) 29-60. doi:10.1007/978-3-540-69248-5\_2.
D. Dempsey et al.,Nicotine metabolite ratio as an index of cytochrome P450 2A6 metabolic activity, Clin. Pharmacal. Ther. 76 (1) (2004) 64-72. doi:10.1016/ j. clpt. 2004.02. 011.
G. St. Helen et al., Reproducibility of the nicotine metabolite ratio in cigarette smokers, Cancer Epidemiol. Biomarkers Prev. 21 (7) (2012) 1105-1114., doi:10.1158/1055-9965.EPI-12-0236.
J. Bloom, et al. The contribution of common CYP2A6 alleles to variation in nicotine metabolism anlong European-Americans, Pharmacogenet. Genomics 21 (7) (2011) 403-416. doi:10.1097/FPC. Ob013e328346e8c0.
N. L. Benowitz et al., CYP2A6 genotype and the metabolism and disposition kinetics of nicotine, Clin. Pharmacol. Ther. 80 (5) (2006) 457-467. doi: 10.1016/j.clpt.2006.08.011.
M. Haberl et al., Three haplotypes associated with CYP2A6 phenotypes in Caucasians, Pharmacogenet. Cenomics 15 (9) (2005) 609-624.
M. Wortham et al., Ex-pression of constitutive androstane receptor, hepatic nuclear factor 4 alpha, and P450 oxidoreductase genes determines interindividuai variability in basal expression and activity of a broad scope of xenobiotic metabolism genes in the human liver, Drug fvletab. Dispos. 35 (9) (2007) 1700-1710. doi:10. 1124/dmd.107. 016436.
H. Z Ring, et al., Gene-gene interactions between CYP2B6 and CYP2A6 in nicotine metabolism, Pharmacogenet. Genomics 17 (12) (2007) 1007-1015.
A. J. Bloom et al., CYP2B6 non-coding variation associated with smoking cessation is also associated with differences in allelic expression, splicing, and nicotine metabolism independent of common amino-acid changes, PLoS One 8 {11} (2013) e79700. doi: 10.1371/ journal.pone. 0079700.
A. J. Bloom et al., The contribution of common UGT2B10 and CYP2A6 alleles to variation in nicotine glucuronidation among european americans, Phannacogenet. Genontics 23 {12} (2013) 706-716. doi:10.1097I FPC.0000000000000011.
A. J. Bloom et al., Effects upon in-vivo nicotine metabolism reveal functional variation in FM03 associated with cigarette consumption, Pharmacogenet. Genomics 23 (2) (2013) 62-68. doi:10.1097/FPC. Ob013e32835c3b48.
S. E. Murphy et al., Nicotine n-glucuronidation relative to n-oxidation and c-oxidation and UCT2B10 genotype in five ethnic/racial groups, Carcinogenesis 35 (11) (2014) 2526-2533. doi:10.1093/carcin/bgu191.
Y. M. Patel et al., The contribution of common genetic variation to nicotine and cotinine glucuronidation in multiple ethnic/racial populations, Cancer Epidemiol. Biornarkers Prev. 24 (1) (2015) 119-127. doi:10.1158/1055-9965. EPI-14-0815.

J.A. Tanner et al., Predictors of variation in CYP2A6 mRNA, protein, and enzyme activity in a human liver bank Influence of genetic and nongenetic factors, J. Pharmacol. Exp. Ther. 360 (1) (2017) 129-139.
E. J. Perez-Stable et al., Nicotine metabolism and intake in black and white smokers, JAIVIA 280 (2) (1998) 152-156.
N. L. Benowitz et al., Slower metabolism and reduced intake of nicotine from cigarette smoking in Chinese-Americans, J. Natl. Cancer Iust. 94 (2) (2002) 108-115.
P. Fagan et al., Biomarkers of tobacco smoke exposure in racial/ethnic groups at high risk for lung cancer, Atn. J. Public Health 105 (6) (2015) 1237-1245. doi:10.2105/AJPH.2014.302492.
H. Wang et al., Associations between genetic ancestries and nicotine metabolism biornarkers in the multiethnic cohort study, Am. J. Epidemiol. 182(11) {2015) 945-951. doi:10.1093/aje/kwv138.
M. J. Chenoweth et al., Known and novel sources of variability in the nicotine metabolite ratio in a large sample of treatment-seeking smokers, Cancer Epidemiol. Biornarkers Prev. 23 (9) (2014) 1773-1782. doi:10.1158/1055-9965. EPI-14-0427.
C. Lerman et al., Genetic variation in nicotine metabolism predicts the efficacy of extended-duration transdermal nicotine therapy, Clin. Pharmacol. Ther. 87 (5) (2010) 553-557. 62o doi: 10. 1038/ clpt. 2010.3.
Schnoll et al., Nicotine metabolic rate predicts successful smoking cessation with transdermal nicotine: a validation study, Pharmacol. Biochem. Behav. 92 (1) (2009) 6-11.
Patterson et al., Toward personalized therapy tor smoking cessation: a randomized placebo-controlled trial of bupropion, Clin. Pharmacol. Ther. 84 (3) (2008) 320-325.
Ho et al., Association of nicotine metabolite ratio and CYP2A6 genotype with smoking cessation treatment in African-American light smokers, Clin. Pharmacol. Ther. 85 (6) (2009) 635-643. doi: 10 .1038/clpt. 2009.19.
Chen et al., Pharmacotherapy effects on smoking cessation vary with nicotine metabolism gene (CYP2A6), Addiction 109 (1) (2014) 128-137. doi:10 .1111/add. 2353.
Lerman et al., PGRN-PNAT Research Group, Use of the nicotine metobolite ratio as a genetically informed biomarker of response to nicotine patch or varenicline for smoking cessation: a randomised, double-blind placebo-controlled trial, Lancet Respir Med 3 (2) (2015) 131-138. doi:10. 1016/82213-2600 (14) 70294-2.
How Tobacco Smoke Causes Disease: The Biology and Behavioral Basis for Smoking-attributable Disease: a Report of the Surgeon General, U.S. Department of Health and Human Services, Public Health Service, Office of the Surgeon General, 2010.
Bush et al., Chapter 11: Genome-wide association studies, PLoS Comput. Biol. 8 (12) (2012) e1002822.
Baurley et al., Genome-Wide association of the Laboratory-Based nicotine metobolite ratio in three ancestries, Nicotine Tob. Res. 18 (9) (2016) 1837-1844.
Patel et al., Novel association of genetic markers affecting CYP2A6 activity and lung cancer risk, Cancer Res. 76 (19) (2016) 5768-5776.
Whirl-Carrillo, et al., Pharmacogenomics knowledge for personalized medicine, Clin. Pharmacol. Ther. 92 (4) (2012) 414-417.
Neter et al., Applied linear statistical models, vol. 4, Irwin Chicago, 1996.
Hesterberg et al., Least angle and11 penalized regression: A review, Statistics Surveys 2 (2008) 61-93.
Kyung et al., Penalized regression, standard errors, and bayesian lassos, Bayesian Analysis 5 (2) (2010) 369-411.
Tibshirani et al., Journal of the Royal Statistical Society. Series B (Methodological) (1996) 267-288.
Hoerl et al., Ridge regression, in 'encyclopedia of statistical sciences', vol. 8 (1988).
Zou et al., Regularization and variable selection via the elastic net, Journal of the Royal Statistical Society: Series B (Statistical Methodoogy) 67 (2) (2005) 301-320.
Friedman et al., The elements of statistical learning, vol. 1, Springer series in statistics New York, 2001.
Hoeting et al., Bayesian model averaging: a tutorial, Statistical science (1999) 382-401.

(56) References Cited

OTHER PUBLICATIONS

Caruana et al., Ensemble selection from libraries of models, in: Proceedings of the twenty-first international conference on Machine learning, AC:tvf, 2004, p. 18.
Wasserman, Bayesian model selection and model averaging, Journal of mathematical psychology 44 (1) (2000) 92-107.
Baurley et al., Discovery of complex pathways from observational data, Stat. Med. 29 (19) (2010) 1998-2011.
Patkar et al., Alterations in tryptophan and purine metabolism in cocaine addiction: a metabolomic study, Psychopharmacology 206 (3) (2009) 479-489.
Cho, et al., Exploratory metabolomics of biomarker identification for the internet gaming disorder in young Korean males, J. Chromatogr. B Analyt. Technol. Biomed. Life Sci. 1057 (2017) 24-31.
Foulds et al., Dimensional personality traits and alcohol treatment outcome: a systematic review and meta-analysis, Addiction 112 (8) (2017) 1345-1357.
Bogdan et al., Imaging genetics and genomics in psychiatry: A critical review of progress and potential, Bio. Psychiatry 82 (3) (2017) 165-175.
Ramsey, Integration of technology-based behavioral health interventions in substance abuse and addiction services, Int. J. Ment. Health Addict. 13 (4) (2015) 470-480.
Agrawal et al., Meta-Analyses of Genome—Wide association data hold new promise for addiction genetics, J. Stud. Alcohol Drugs 77 (5) (2016) 676-680.
Acion et al., Use of a machine learning framework to predict substance use disorder treatment success, PLoS One 12 (4) (2017) e0175383. doi:10. 1371/journal.pone.0175383.
Chih et al., Predictive modeling of addiction lapses in a mobile health application, J. Subst. Abuse Treat. 46 (1) (2014) 29-35. doi:10. 1016/j . jsat. 2013. 08. 004.
Zong et al., Deep mining heterogeneous networks of biomedical linked data to predict novel drug-target associ-ations, Bioinformatics 33 (15) (2017) 2337-2344.
Institute of Medicine, Committee on Developing Biomarker-Based Tools for Cancer Screening, Diagnosis, and Treatment, Cancer Biomarkers: The Promises and Challenges of Improving Detection and Treatment, National Academies Press, 2007.
Committee on the Review of Omics-Based Tests for Predicting Patient Outcomes in Clinical Trials, Board on Health Care Services, Board on Health Sciences Policy, Institute of Medicine, Evolution of Translational Ornics: Lessons Learned and the Path Forward, National Academies Press, 2012.
McShane et al., Criteria for the use of omics-based predictors in clinical trials, Nature 502 (7471) (2013) 317-320. doi: 10 .1038/nature12564.
McShane et al., Criteria for the use of omics-based predictors in clinical trials: explanation and elaboration, BMC Med. 11 (2013) 220. doi: 10.1186/1741-7015-11-220.
McGinnis et al., Best care at lower cost: the path to continuously learning health care in America, National Academies Press, 2013.
Berger, Genomics-enabled learning health care systems: Gathering and using genomic information to improve patient care and research: Workshop summary, National Academies Press, 2015.
Kranzler et al., Precision medicine and pharmacogenetics: what does oncology have that addiction medicine does not?, Addiction 112 (12) (2017) 2086-2094.
Salgado et al., IBCD—Faculty, Societal challenges of precision medicine: Bringing order to chaos, Eur. J. Cancer 84 (2017). 325-334.
Amur et al., Biomarker qualification: Toward a multiple stakeholder framework for biomarker development, regulatory acceptance, and utilization, Clin. Pharmacol. Ther. 98 (1) (2015) 34-46.
Sauer et al., Biomarker Programs, Predictive Safety Testing Consortium, Preclinical biomarker qualification, Exp. Bioi. Nied. (2017) 1535370217743949.
Amur et al., Building a roadmap to biomarker qualification: challenges and opportunities, Biomark. fed. 9 (11) (2015) 1095-1105.
Bough et al., Biomarkers for smoking cessation, Clin. Pharmacol. Ther. 93 (6) (2013) 526-538.
Bough et al., Biomarkers for the development of new medications for cocaine dependence, Neuropsychopharmacology 39 (1) (2014) 202-219.
Dobson, An Introduction to Generalized Linear Models, Third Edition, Taylor & Francis, 2008.
Zou et al., The adaptive lasso and its oracle properties, Journal of the American statistical association 101 (476) (2006) 1418-1429.
Fan et al., Variable selection via nonconcave penalized likelihood and its oracle properties, Journal of the American statistical Association 96 (456) (2001) 1348-1360.
Zhang et al., Nearly unbiased variable selection under minimax concave penalty, The Annals of statistics 38 (2) (2010) 894-942.
Breheny et al., Coordinate descent algorithms for nonconvex penalized regression, with applications to biological feature selection, The annals of applied statistics 5 (1) (2011) 232.
Candes et al., The dantzig selector: Statistical estimation when p is mich larger than n, The Annals of Statistics (2007) 2313-2351.
Li et al., The flare package for high dimensional linear regression and precision matrix estimation in r, The Journal of Machine Learning Research 16 (1) (2015) 553-557.

\* cited by examiner

Biosignature learning

|   | $C_1$ | $C_2$ | $C_{p1}$ | $G_1$ | $G_2$ | $G_3$ | $G_{p2}$ |
|---|---|---|---|---|---|---|---|
|   | 1 | 0 | ... | 0 | 2 | 0 | ... |
|   | 0 | 1 |   | 2 | 1 | 0 |   |
|   | 1 | 0 |   | 0 | 2 | 2 |   |
|   | 1 | 0 |   | 1 | 0 | 0 |   |

Z

Biosignature applications

|   | $C_1$ | $C_2$ | $C_{p1}$ | $G_1$ | $G_2$ | $G_3$ | $G_{p2}$ |
|---|---|---|---|---|---|---|---|
|   | 1 | 0 |   | 0 | 2 | 0 |   |
|   |   | 1 |   | 1 | 0 | 0 |   |
|   |   | 1 |   | 0 | 2 | 2 |   |
|   | 1 | 1 |   | 0 | 2 | 2 |   |

Predict Z using learned biosignatures $Z_{pred}$

BIOSIGNATURE DISCOVERY FOR SUBSTANCE USE DISORDER USING STATISTICAL LEARNING

CROSS-REFERENCE TO RELATED APPLICATION

This patent application claims the benefit of U.S. Provisional Patent Application Ser. No. 62/625,717, entitled "Genomic Predictions of Nicotine Biomarkers, Smoking Cessation, and Tobacco Related Diseases," filed Feb. 2, 2018, which this application is incorporated in its entirety here by this reference.

TECHNICAL FIELD

This invention relates to a system and method for discovery of biomarkers in the field of substance use disorders. This invention applies statistical learning models in a unique way to create a more accurate method for recognition of biomarkers to assist in the treatment of substance use disorders. The biomarkers discovered with this invention will be used to evaluate risk and exposure for substance use disorders.

BACKGROUND

There are limited biomarkers for substance use disorders (SUDs). Traditional statistical approaches identify simple biomarkers in large samples, but clinical use cases are still being established. High-throughput clinical, imaging and "omic" technologies are generating data from SUD studies and may lead to more sophisticated and clinically useful models. However, analytic strategies suited for high dimensional data are not regularly used. We review strategies for identifying biomarkers and biosignatures from high dimensional data types. Focusing on penalized regression and Bayesian approaches, we address how to leverage evidence from existing studies and knowledge-bases, using as an example, nicotine metabolism.

SUMMARY

Biosignatures in Substance Use Disorders

Biomarkers for substance use disorders (SUD) are available for drug use based on detection of the substance or its metabolites, e.g., ethyl glucuronide for alcohol, tetrahydrocannabinol for marijuana, and cotinine for tobacco. They are not, however readily available for the neurobiological modifications that result in the maladaptive behaviors we describe as addiction. Clinical phenotyping has been used to assess the presence and severity of SUDs and comorbid psychiatric disease and to evaluate treatment options. Some embodiments of this invention may use massive data on patients with SUDs (e.g., genomics and other omics (see Glossary), and imaging on the structure and function of the brain). The ability to combine omics with each other and with complex neurocognitive or imaging data promises to deliver biosignatures that will reflect the behavioral and biological modifications that occur in addiction. Standard biostatistical analysis that has been so useful in clinical research does not perform well in this high dimensional environment where variables vastly outnumber patients. Studies of SUDs and treatments are beginning to use more comprehensive modeling approaches. In some embodiments, data from diverse concepts (brain, personality, cognition, demographics, and genetics) may be incorporated into a highly predictive model of current and future alcohol abuse in adolescents. In other embodiments, researchers perform an integrative analysis to link genomic variation with expression changes in brains of alcohol dependent individuals.

Biosignature discovery provides a way of combining many variables (e.g., genetic effects, voxels in neuroimaging) into meaningful models. Without models of net effects, it is difficult to interpret many small effects, especially given complex correlations in data. High dimensional data is also becoming quite common on large populations, while measures of molecular phenotypes, which may not be cost effective or safely accessed, are less commonly collected. Bio-banks of large cohorts with genomic data are becoming available, such as the Millions Veteran's Program, the All of Us Research Program, UK Biobank, GenomeAsia 100K, and even direct-to-consumer services such as 23andMe and Helix. While there is recognition that additional omics are necessary to understand the influence of genotype on phenotype, the most commonly available data will remain genotypic. Using a biosignature approach, there are opportunities to gain new biological insights and assess multiple predicted phenotypes. This is one of the premises behind transcriptome-wide association studies using genome-wide genotype data. Using studies where both genomic and transcriptomic data are available, the tissue-specific relationship between DNA (genotypes) and RNA (gene expression) can be modeled to generate predictive models. These models are then used in genomic data to predict expression and association to diseases or quantitative traits.

The overall strategy of using high dimensional data to profile and predict molecular phenotypes and other outcomes is a new development path for biomarkers and biosignatures for SUDs and their treatments (see FIG. 1). Discovery is driven by statistical learning algorithms suited for detection of biosignatures from high dimensional data. The learned biosignatures are then validated and applied in various use-cases (e.g., to identify subgroups at risk of SUDs or as tools to optimally select treatments). In some embodiments data is propagated from new observations and the predictive performance of the models back into the development cycle to allow for continuous improvement of the biosignatures (FIG. 1).

Application to Nicotine Metabolism

We use, for example, the nicotine metabolism pathway as a motivating example for the utility of statistical learning to discover and use SUD biosignatures from high dimensional data. Nicotine metabolism is strongly influenced by genes; the majority of variance (approximately 74%) may be due to additive genetic influence. The cytochrome P450 monooxygenase 2A6 (CYP2A6) is the dominant but not exclusive metabolic enzyme in nicotine metabolism. The ratio of the first two major metabolites of nicotine (trans-3'hydroxycotinine/cotinine, or the nicotine metabolism ratio; NMR) can serve as a biomarker of nicotine metabolism. The NMR is estimated biochemically or via prediction using CYP2A6 genotypes. Genes coding for numerous additional oxidases (FMO3, AO, CYP2B6, POR, AKR1D1), and the uridine diphosphate glycosyltransferases (UGTs), have been found to be associated with nicotine metabolism through individual candidate gene single nucleotide polymorphisms (SNPs), or, less commonly, gene/protein expression, or protein activity analyses. Moreover, in diverse populations and using blood, saliva and urine biospecimens from smokers, or using labeled nicotine and cotinine in clinical laboratory studies using blood and urine, nicotine metabolism has been reported to vary by ancestry, age, gender, body mass index, estrogenic hormones, alcohol and cigarette consumption.

In addition to pharmacologic investigations of nicotine metabolism, investigators have studied the influence of nicotine metabolism on smoking cessation retrospectively, using either the biochemical measure of the NMR or genotypes associated with reduced NMR. There has been one prospective analysis of the influence of the NMR on smoking cessation, examining the efficacy of nicotine replacement therapy (NRT), varenicline (VAR) and placebo in slow and normal nicotine metabolizers, with the NMR determined from direct biochemical measurement. Note that biomarkers of nicotine metabolism, as studied in the literature, have differed somewhat depending upon genotyping approach, biochemical ratios and cutoff-points selected, as well as clinical or population samples used to establish the biomarker; one common dichotomization stratifies individuals with normal metabolism versus slow metabolism.

In general, retrospective studies of smokers, randomized to NRT or placebo, have shown that individuals with biomarkers of slow metabolism, whether defined by genotype or biochemical ratio, were significantly more likely to remain abstinent than individuals with normal metabolism. In one retrospective analysis, individuals with slow nicotine metabolism did not benefit (no reduction in relapse proportions) from active treatment (NRT, bupropion or combined active treatment) compared to placebo treatment, while individuals with fast nicotine metabolism did benefit from active treatment. In the prospective trial stratified by the NMR, individuals with normal nicotine metabolism responded significantly better to active treatment than placebo, and those randomized to varenicline (VAR) responded significantly better than those randomized to NRT. Together, these findings suggest that treatment success can be optimized by assigning treatment to patients by their NMR status, e.g., assigning more active pharmacotherapy to normal metabolizers and less active pharmacotherapy to slow metabolizers.

In some embodiments the results and data described above can be directly used in biosignature development (FIG. 1). Statistical learning algorithms (described in the next sections) can be applied to detected biosignatures of nicotine metabolism. These biosignatures (once validated) can be used to predict other outcomes (such as smoking cessation) or to personalize treatments (e.g., bupropion, varenicline, or NRT for a smoker; FIG. 1).

Biosignature Detection in High Dimensional Data

The data layout for biosignature learning is shown in FIG. 2. One or more SUD studies have both high dimensional data (e.g., genomic) and molecular phenotypic data (e.g., metabolites). For simplicity, it was assumed that the clinical factors were binary and that the genotypes were single nucleotide polymorphisms (SNPs), coded by the number of copies of the minor allele. Millions of genotyped and imputed SNPs can be available. The relevant variables (the biosignature) and its net effects on a predictable molecular phenotype (FIG. 2) are then learned using statistical algorithms. Once the relationships are represented in models, they can be applied to new data for prediction and assessment of the outcomes of interest (FIG. 2). For nicotine metabolism, these may be smoking cessation, lung cancer risk, treatment response, etc. Of note, the molecular phenotype does not need to be measured once the model is learned, as it can be predicted from the biosignature, sometimes from summary statistics.

Simple models consider only one genetic variant at a time. A genome-wide association scan (GWAS) across the genome represents millions of tests for genetic associations with the trait or outcome. There have been four GWASs using the NMR as the trait to date. These four GWASs used readily available GWAS genotyping arrays, as well as typical statistical pipelines for genotype cleaning and imputation via the 1000 Genomes Project resource (http://www.1000genomes.org). Two GWASs represented meta-analyses of single ancestries, one was a multi-ancestry meta-analysis, and one was a multi-ancestry mega-analysis. As expected, in all four scans, variants in and near CYP2A6 on human chromosome 19 (the gene encoding the primary nicotine metabolic enzyme) were associated with the NMR at genome-wide significance. In each GWAS, the most significant associations were located proximal, within and distal to CYP2A6, with individual SNPs, significance ranks and span of association being dependent upon study, sample size and ancestry composition. We and others have noted complex patterns of association with the NMR that span into nearby genes, including CYP2B6 (FIG. 3). In some embodiments of this invention, biosignatures of nicotine metabolism are defined based on genomic data to overcome complex patterns of marginal associations even though the number of variables exceed the sample size (known in statistics as P>N).

In some embodiments, with available genome-wide data from our GWAS, we may select 11 genomic regions implicated in nicotine metabolism for modeling. We may identify the relevant regions using a combination of knowledge bases (such as PharmGKB) and recent literature. The second strategy consists of using algorithms to reduce model complexity. The rationale here was that there can be too many variables for a human to decide which should go in a model.

Two classes of statistical learning algorithms may be used for selecting which variables should be in a model and estimating its joint effects on an outcome. These algorithms explore a trade-off between model complexity, prediction bias, and prediction variance. That is, prediction bias can be reduced by increasing model complexity. Alternatively, one can also trade prediction bias for reduced variance using approaches to reduce complexity. The goal is to find a sweet spot, selecting the right model complexity to minimize prediction error.

BRIEF DESCRIPTION OF DRAWINGS

FIG. 2 shows biosignatures of nicotine metabolism.

DETAILED DESCRIPTION OF THE INVENTION

Figure 1:
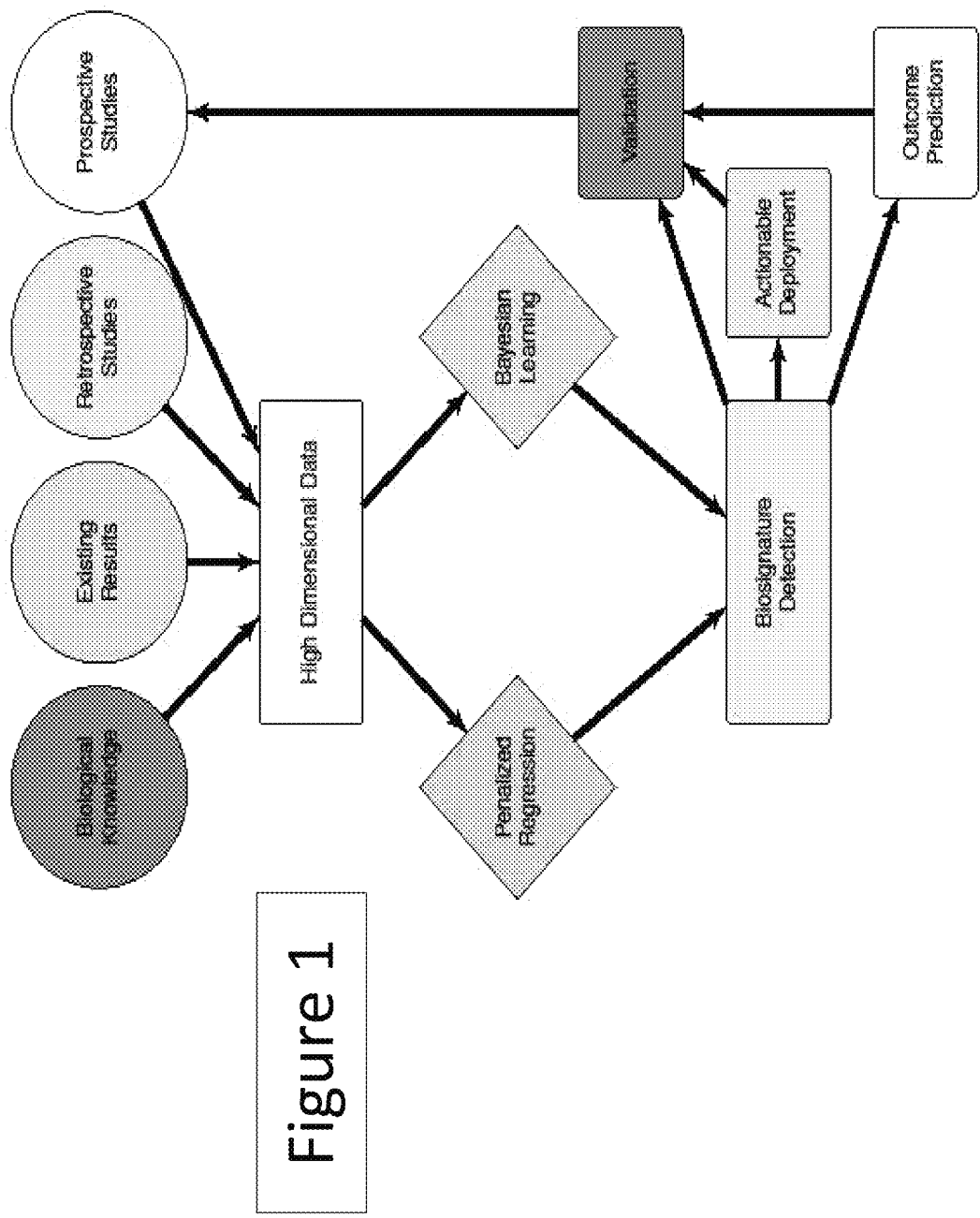
FIG. 1 shows a biosignature development workflow.

The detailed description set forth below in connection with the appended drawings is intended as a description of presently-preferred embodiments of the invention and is not intended to represent the only forms in which the present invention may be constructed or utilized. The description sets forth the functions and the sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

The First Approach: Penalized Regression

Penalized regression approaches add a penalty term to the typical optimization problem. That is, many penalized regression methods estimate the regression coefficients by minimizing a penalized residual sum of squares which is given by:

$$\hat{\beta} = \underset{\beta}{\operatorname{argmin}} \sum_{i=1}^{N} \left( y_i - \beta_0 - \sum_{j=1}^{P_1} \beta_{1j} C_{ij} - \sum_{j=1}^{P_2} \beta_{2j} G_{ij} - \sum_{j=1}^{P_3} \beta_{3j} Z_{ij} \right)^2 + P(\beta, \lambda),$$

where $\lambda$ represents a collection of tuning parameters which implicitly controls the model complexity, $\beta$ denotes the collection of all the regression coefficients, and $P(\bullet, \bullet)$ is a penalty function. For example, a penalty function of the form $$P(\beta, \lambda) = \lambda_1 \alpha \sum_{k=1}^{3} \sum_{j=1}^{P_k} |\beta_{kj}| + \lambda_2 (1-\alpha) \sum_{k=1}^{3} \sum_{j=1}^{P_k} \beta_{kj}^2,$$

may be considered, where setting $\alpha=1$ results in the least absolute shrinkage and selection operator (LASSO) of, $\alpha=0$ provides the usual ridge estimator, and $\alpha \in (0,1)$ results in the elastic net of. In general, through regularization, the ridge estimator may be able to provide better prediction performance by exploiting the so called bias versus variance trade-off, and can be used (unlike standard ordinary least squares) to uniquely estimate the regression coefficients when P>N. Unlike ridge, LASSO techniques may provide a parsimonious model through automatic variable selection, though it has been empirically shown that ridge maintains a higher level of prediction accuracy in the face of correlated predictors, when compared to LASSO. The elastic net is a blend of ridge and LASSO, which attempts to gain from their strengths and overcome their individual weaknesses. In particular, the elastic net makes use of a linear combination of the ridge and LASSO penalties and can therefore complete automatic variable selection while maintaining a high degree of prediction accuracy in the face of correlated predictors.

Different penalized regression procedures can be applied to the motivating nicotine metabolism data; for details on these algorithms, their implementation, and their penalty structures see Table 1. In particular, Table 1 provides nine different penalized regression methods, citations that present the relevant background on each procedure, and R-packages that can be utilized to implement each of the methods. As discussed above, these algorithms have different properties and therefore provide diverse insights into the data. We believe that the collection of models (the ensemble) characterizes the biosignature of this molecular phenotype. This is demonstrated in FIG. 4, where the rows represent the biosignatures learned by the different algorithms applied to the nicotine metabolism data. The un-shaded portions represent the genetic signature identified by each approach. As expected, a handful of SNPs (out of 3752) were selected in all the models. The largest model included 63 SNPs, but more parsimonious models explained NMR just as well with fewer SNPs (58-62% NMR). The genetic biosignature found by these methods in human chromosome 19 are overlayed on the marginal results in FIG. 3. This highlights additional signals near the CYP2A6 and CYP2B6 genes that may have been missed in a more traditional approach. The collection of variables that is predictive of an individual's nicotine metabolism is more than those discoverable using standard genetic association scans. To predict nicotine metabolism with new genotypes, one simply applies the learned weights to the SNP biosignatures. The predicted nicotine metabolism can be then applied in additional association or clinical studies.

The differences in the SNPs selected by the penalized regression algorithms (FIG. 4) suggest that there are multiple "good" models and one may want to average over the strengths of a set of models when making predictions. This leads to the second approach where model uncertainty can be quantified.

The Second Approach: Bayesian Model Averaging

In the previous section we discussed the uncertainty with which SNPs belong in a biosignature of nicotine metabolism. Bayesian approaches can account for this uncertainty in the model specification. Here, the posterior probability for a given model is:

$$p(M|D) = \frac{p(D|M)p(M)}{\sum_{m \in M} p(D|m)p(m)}$$

Obtaining the denominator would involve exploring all possible biosignatures which may not be computationally feasible. Thus the posterior probability is usually approximated by assessing the relative merit of a subset of models. The likelihood above is actually marginalized over the parameters in the model and again is often approximated.

$$p(D|M) = \int_\beta p(D|\beta,M)p(\beta)d\beta$$

The priors on the model $p(M)$ and its parameters $p(\beta)$ can give us the opportunity to formally introduce existing results, knowledge-bases, and assumptions into the modeling; e.g., what variables are biologically important, the direction and magnitude of their importance, and the certainty with which they are involved. In fact, most penalized regression approaches 242 can also be represented by specifying priors on $p(\beta)$.

Figure 5:
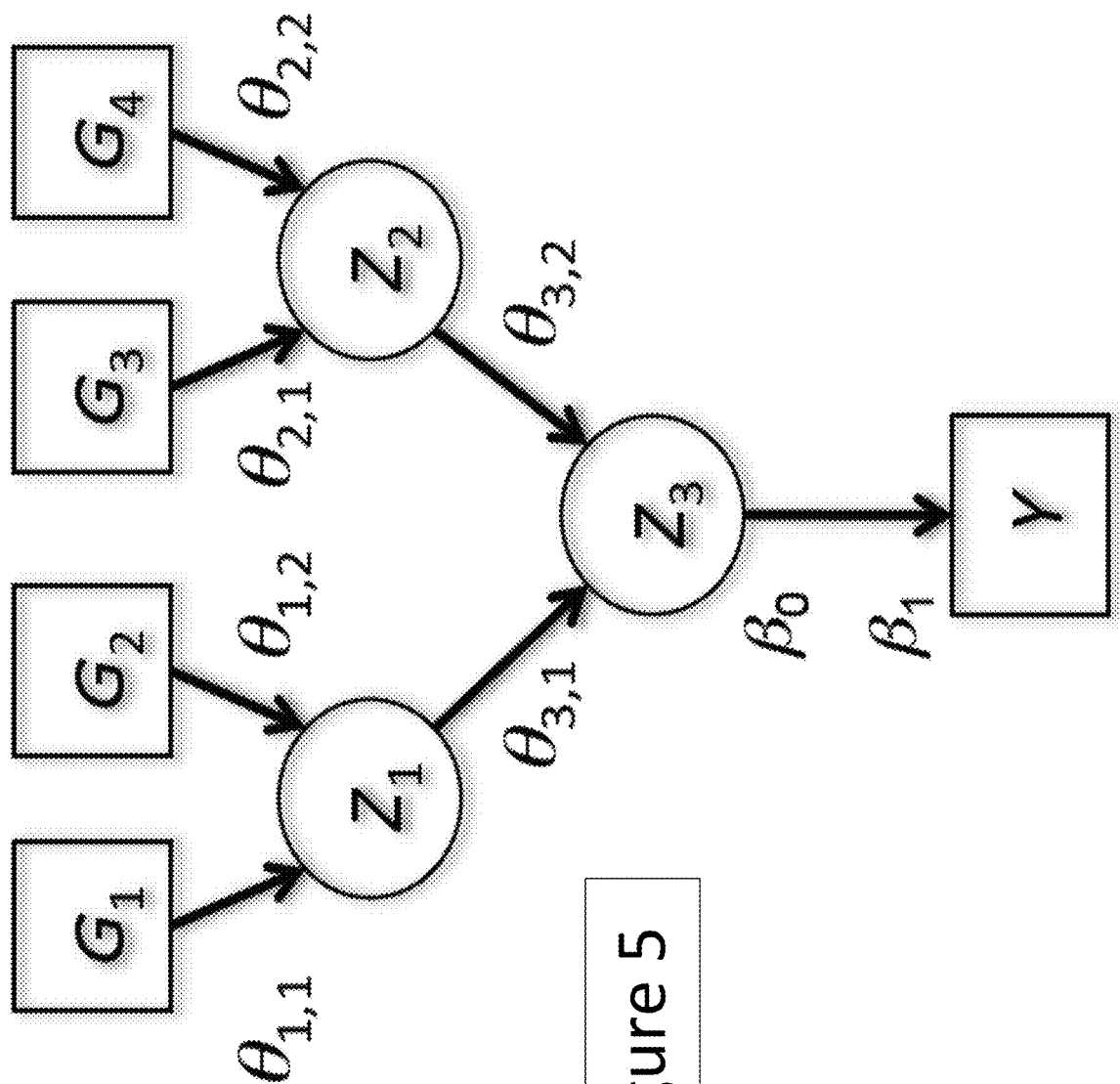
FIG. 5 shows tree-based structures representing complex relationships in sets of variables.

More complex relationships among variables can also be learned from the data. Combinations of SNPs or other factors can be condensed into new derived variables $Z_j$. For example, tree structures denoted $\Lambda$, can be considered where the output of each node is determined by its input values and a set of edge parameters. One such tree structure is shown in FIG. 5, which represents the following system of equations:

$$Z_1 = \theta_{1,1} G_1 + \theta_{1,2} G_2 + (1 - \theta_{1,1} - \theta_{1,2}) G_1 G_2 \quad \text{a.}$$

$$Z_2 = \theta_{2,1} G_3 + \theta_{2,2} G_4 + (1 - \theta_{2,1} - \theta_{2,2}) G_3 G_4 \quad \text{b.}$$

$$Z_3 = \theta_{3,1} Z_1 + \theta_{3,2} Z_2 + (1 - \theta_{3,1} - \theta_{3,2}) Z_1 Z_2 \quad \text{c.}$$

These tree-based derived variables provide a very flexible way of representing interactions. For example, given binary inputs, different edge parameters can represent different operators. If $\theta_1=\theta_2=0.5$, the effects are additive; if $\theta_1=\theta_2=0$ there is an effect only when both variants are present (logical AND); and if $\theta_1=\theta_2=1$ there is an effect if either variant is present (logical OR). The effects of the derived variables represent the net effect of the tree.

Figure 6:
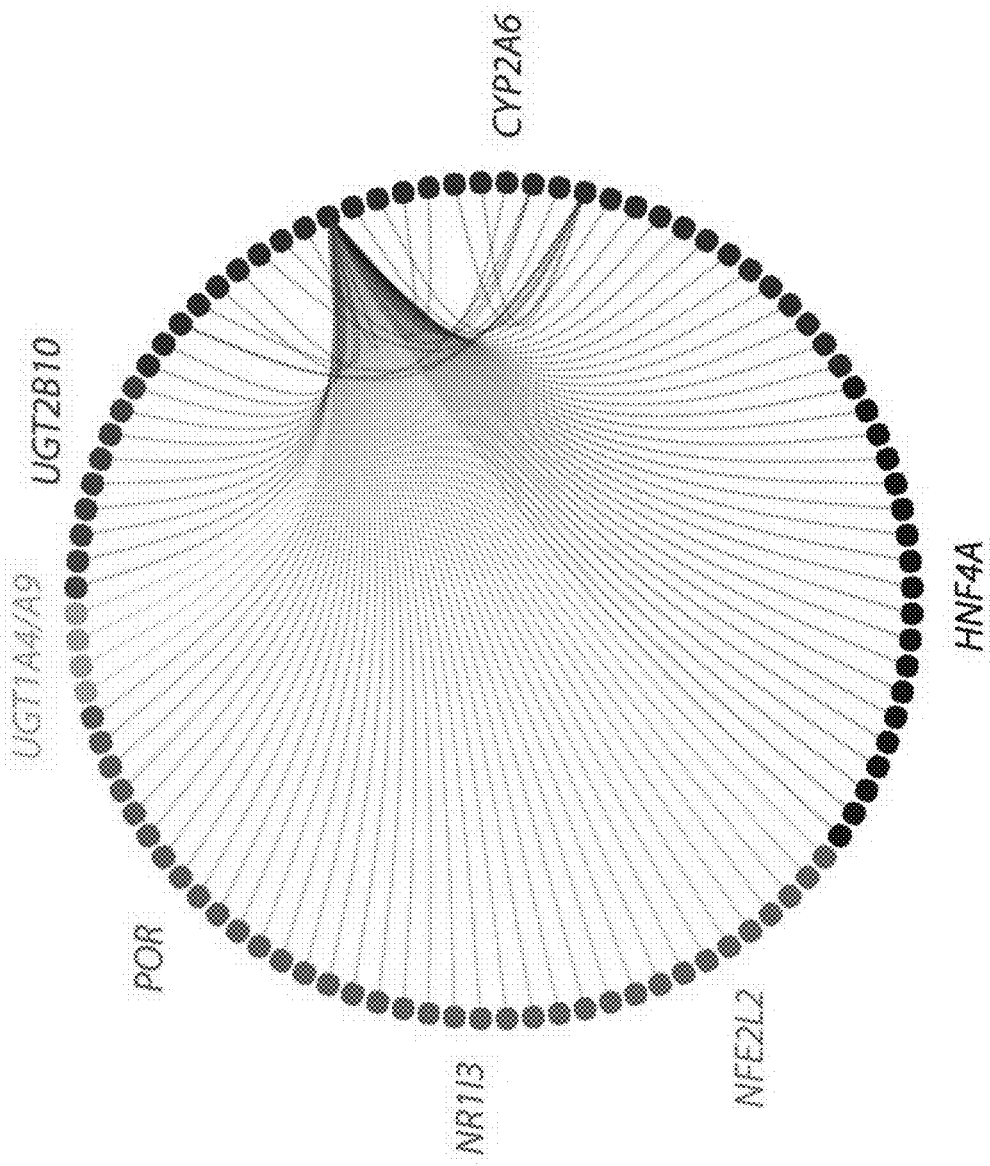
FIG. 6 shows joint SNP effects on nicotine metabolism.

Under this theme, every pairwise SNP effect on nicotine metabolism can be considered (over 6 million derived variables). The evidence for or against each can be computed using Bayes factors, the ratio of posterior to prior odds. The top associations are shown in FIG. 6. Seven genomic regions showed evidence of interactions. The CYP2A6 region is an important hub, with other genetic variants near UGT2B10, UGT1A4/A9, POR,NR1I3, NFE2L2, and HNF4A, contributing to its effects on nicotine metabolism (FIG. 6).

More complex combinations (starting with one tree and then modifying it in a quest to find better combinations) can be sought. This process can be repeated hundreds of thousands of times. Combinations of variants that had large impacts on nicotine metabolism were found. For example, the best learned model had a posterior probability of 0.90%, explained 43% of nicotine metabolism, and had a rather large effect on natural log NMR ($\beta_A=-1.35$). As in penalized regression, multiple models fit the data well, but the posterior probabilities provide an intuitive way to average models. Trees with the highest posterior probabilities contained a handful of SNPs and had strikingly similar measures of fit. This suggest that one should make nicotine metabolism predictions by averaging over the collection of models. The posterior predictive distribution allowed us to generate predictions of new observations using the entire distribution of explored biosignatures.

Incorporating these Approaches into Research and Clinical Translation

Statistical learning algorithms can help identify biosignatures of SUD outcomes. Once learned, these models can provide biological insights on their own as well as be applied to existing or new data to generate predictions. With the focus of the nicotine metabolism application in this example relied on genomics, the approach can be applied to other data commonly available or becoming available in studies of substance use disorders, such as metabolomics, personality assessment, neuroimaging, and mobile health applications. The first strategy described involves learning using penalized regression algorithms. These algorithms select variables while simultaneously estimating their effects. As demonstrated in the nicotine metabolism application, they extract different features from the data. We advocate using the entire ensemble to characterize SUD biosignatures because each algorithm can extract unique features in the data. The second approach involves learning a distribution of models and leveraging that distribution in prediction. These Bayesian algorithms allow us to consider more complex relationships among variables. In the nicotine metabolism example, variants near CYP2A6 and other parts of the pathway jointly influenced nicotine metabolism (FIG. 6). This suggests that learning algorithms can identify combinations of genetic variances that explain molecular phenotypes that may be missed using traditional analyses. The next steps involve: validating the biosignatures in other datasets with both genomic data and nicotine metabolites, and then applying the learned biosignatures and weights in other datasets, to observe how the biosignatures influence smoking related outcomes (e.g., smoking-related behaviors, cessation, disease and comorbidities).

Many statistical learning approaches have been around for some time, but are just now being applied to SUDs. Computing used to be a major bottleneck in applying these algorithms. But with new acceleration computing and software stacks, algorithms are being retooled to handle much more complex and large datasets. As in all industries, data is now in abundance. There are more data on individuals with SUDs available now than ever before. Several groups have begun to explore applying these algorithms to learn predictors of response to treatment for SUDs, but this is just the beginning of a new wave of discovery. There has been a recent increase of deep learning algorithms being applied to health applications: automatic detection of new tumors from imaging data, discovery of new drug targets, and precision treatments in cancer patients (http://candle.cels.anl.gov/). The availability of data, computation, and algorithms have profound implications for the future of biosignature and biomarker development in SUD screening, diagnosis, and treatment.

Retrospective biomarker/biosignature discovery has strengths (available data) and weaknesses (older, possibly less relevant trials, biospecimen availability) or biases (lack of biospecimens, older molecular datasets). Similarly, hypothesis-driven prospective biomarker discovery and validation has strengths (ability to define variables/study domains, state of the art biospecimen and biomarker data collection) and weaknesses (candidate hypotheses may miss predictive biomarker variables/domains). The choice of a retrospective versus a prospective approach may depend upon currently available resources or the ability to leverage existing public datasets. A prospective discovery and validation design offers the theoretical ability to include all domains or selected (hypothesis-driven) domains; the former is limited by practical considerations and the latter may unfortunately restrict variable discovery. The necessity of validation for replication, and clinical utility analysis to fulfill regulatory and reimbursement requirements, means that designing discovery and validation studies will involve both retrospective and prospective designs. Excluding logical incompatibilities, practical and contingent limitations are more likely to limit or slow biosignature development and translation to practice than the choice of study design or whether either type of design is hypothesis-driven.

Guidelines for biomarker development and translation to treatment of omics-based tests has been a hot topic for almost a decade. Omics-based tests are defined as an assay composed of or derived from many molecular measurements and interpreted by a fully specified computational model to produce a clinically actionable result. There are currently no regulatory guidelines on versioning of biosignatures whose specifications may adapt and improve with more data (FIG. 1). Current guidelines require that biomarker tests for any application be fixed before moving into a clinical trial for assessment of their utility. Current recommendations regarding evaluating evidence on a biomarker prior to final utility testing are focused on the limitations derived from development from retrospective analyses, the complexity of the bioassay, and the nature of the mathematical model. Many challenges remain in the translation of biosignatures to clinical care; the guidelines, roadmap, and regulatory ecosystem will need to be recalibrated as models and predictions become more dynamic.

Some progress has been made in developing dynamic systems that collect and analyze data from its own processes in order to improve outcomes. Recommendations for development of a rapid learning system for biomarkers encompassing policy, data infrastructure and patient care are part of an evolutionary process of the biomedical enterprise. This represents extensions of older ideas of a learning, continuously improving, and, a genomics-enabled learning health care system. Adding biosignature discovery and translation to these ideas implies much greater efforts to align patient care, and provider and health care system practice than introduction of a single biomarker with a single context of use. Rising to the challenges of biosignature translation have perhaps been most thoroughly addressed in oncology. However, the FDA has provided guidance on: the multiple domain challenges; the general pathway for biomarker qualification; and, biomarkers for specific SUDs.

In some embodiments, the penalized regression models may be represented in a Bayesian framework by different specifications of the prior distribution on the beta coefficients. Likewise, Bayesian maximum a priori estimators can be thought of as penalized regression estimators.

Here, new strategies for biosignature development have been described that acknowledge the complexities of disease and data and touch on the ongoing challenges of translation to clinical care. In both biosignature development and in translation to clinical care, complex challenges require comprehensive, integrated solutions. We encourage addiction researchers to share data, organize themselves to enable secondary data analyses, and consider applying these and other learning algorithms to their data to generate new biological insights and prediction models. We realize there are some remaining big questions on how the strategy presented fits into existing biomarker development, clinical translation, and regulation paradigms. There is a delicate balance between encouraging standardization and enabling a learning healthcare system that requires scientific and regulatory leadership to advance biosignatures into clinical care.

EXAMPLE

In the U.S., 1 of every 5 deaths is attributed to smoking-related disease. Reducing smoking prevalence could salvage years of life and a portion of the >289 billion USD in healthcare costs and decreased productivit. Despite 69% of smokers wanting to quit and 52% having made a quit attempt, only 6.2% are successful annually. The poor cessation rates in the general population are attributable to two major factors: best practices for assisting smokers to reach the treatment stage are not fully implemented in health care; and modest and variable performance in therapies for smoking cessation.

Meta-analyses of randomized clinical trials (RCTs) have shown that behavioral counseling, the three FDA approved smoking cessation pharmacotherapies (nicotine replacement therapy (NRT), bupropion (BUP), and varenicline (VAR)), and combination therapies, are significantly more effective than placebo (PLA). Abstinence rates remain low (<37%) at 24 weeks post-treatment for all therapies, both in clinical trials and population-based studies. Even with the best smoking cessation therapy (pharmacotherapy with behavioral support), more than 60% of smokers attempting to quit will relapse within six months. Given these issues, it is not surprising that smoking cessation therapies remain underutilized by U.S. smokers; recent studies found less than 30% used pharmacotherapies, 6% used counseling, and 10% used combined therapies.

In response to this problem, within the last two years, U.S. leaders in preventive, cancer, and psychiatric care introduced guidelines to encourage their colleagues to offer tailored smoking cessation treatments. To varying degrees, these guidelines and the USPHS clinical practice guideline recognize differences in therapy efficacy due to patient characteristics. Three of four guidelines recognize the influence of withdrawal, two recognize comorbidity, and one each recognizes gender, health insurance, and nicotine dependence. However, no guideline recognizes the influence of nicotine metabolism, age, race, employment, education, income level, or genomics.

Our approach to this problem is to acknowledge the importance of individual clinical and genomic factors in smoking cessation. We aim to develop a pharmacogenomic test that can be used to predict a smoker's nicotine dependence and metabolism as well as likelihood of abstinence given available smoking cessation therapies (Smokescreen®TL). Such information will enable personalized medicine, and improve the efficacy of established therapies. To develop this pharmacogenomic test, we propose to focus on the genomics of nicotine metabolism, nicotine dependence and response to smoking cessation therapy.

Nicotine Metabolism

The cytochrome P450 monooxygenase 2A6 (CYP2A6) is the dominant but not exclusive metabolic enzyme in nicotine metabolism. Numerous additional oxidases (FMO3, AO, CYP2B6, POR, AKR1D1), and the uridine diphosphate glycosyltransferases (UGTs), influence nicotine metabolism. An under-examined source of enzymes influencing nicotine metabolism are the regulators of CYP2A6 transcription, such as general hepatic transcription factors, and regulators of stress response. Although nicotine metabolism is a continuous phenotype, many current studies use CYP2A6 haplotypes or diplotypes, or threshold values, to categorize individuals into slow, normal, or fast metabolic strata. Nicotine metabolism varies by ancestry, age, gender, BMI, estrogenic hormones, and substance use. In addition the relation between the NMR and measures of nicotine dependence differ by ancestry.

Biomarker for Smoking Cessation

Lerman et al have examined NRT and VAR efficacy in slow (NMR<0.31) and normal nicotine metabolizers in NCT01314001, with the NMR determined from direct biochemical measurement. Lerman found normal metabolizers responded significantly better to VAR than to NRT, while slow metabolizers experienced significantly more adverse events. Chen et al studied the effect of nicotine metabolism on NRT and BUP efficacy in NCT00332644. Chen estimated nicotine metabolism using the Bloom et al nicotine activity model, stratifying by the lowest quartile versus the upper three quartiles (slow versus fast). Chen et al found that NRT significantly reduced relapse rates for fast but not slow nicotine metabolizers. Lerman suggest that slow nicotine metabolizers benefit more from NRT than normal metabolizers, while Chen suggest that fast metabolizers benefit more from NRT than slow metabolizers. Note that the two ratios of nicotine metabolites used in analysis of NCT01314001 and NCT00332644 are correlated, but differ: the NMR and the Bloom model ratio focus attention on the second and first nicotine C-oxidation steps, respectively. These metabolite ratios differ from each other by the components of the ratios, by the type and number of metabolic steps from other reactions occurring in the pathway, and by their stability and reproducibility. The discordant interpretations that derive from analyses of these two RCTs highlight the need for biomarkers with common data sources, predictors and algorithms. A robust pharmacogenomic test for predicting the NMR will be useful for predicting therapy response.

Nicotine Dependence

The fundamental insight that nicotine intake is both regulated and subject to individual differences was developed >40 years ago, however, elaboration has lagged behind research into nicotine metabolism. Nicotine dependence encompasses both pharmacokinetic and pharmacodynamic regulation of nicotine intake, moderated by pleasurable (rewarding) and nauseating (aversive) responses, in addition to other genetic, environmental and gene-environment factors. Nicotine binds to nicotinic cholinergic receptors (nAChRs), triggering ACh release, and activating neuronal circuits with rewarding and aversive effects, the balance of which regulates nicotine intake.

Genetics has an overarching influence across nicotine dependence: initiation, regular tobacco use and nicotine dependence. The largest meta-GWAS studies identify pharmacokinetic and pharmacodynamic regulators of nicotine pharmacology, including metabolic enzymes of nicotine, oxygen and dopamine, and cholinergic receptors. Gene and pathway level analyses with common measures of nicotine dependence such as cigarettes per day (CPD) in the TAG Consortium, identified 14 genes and 34 pathways at genome-wide significance. Comprehensive curation of human linkage and association studies of nicotine dependence identified 47 genes. Biological functions include metabolism and neuropharmacology of nicotine, rewarding and aversive pathways, neuronal functions, circadian signaling, and neurotransmitter metabolism.

Biomarker for Smoking Cessation

Retrospectively, nicotine dependence measures have been shown to predict abstinence. The top ranked gene influencing cigarette consumption and nicotine intake in the genome is CHRNA5 on chr15q25.1. A biomarker of nicotine dependence, baseline carbon monoxide level (associated with CHRNA5), was used to prospectively stratify smokers prior to randomization in RCT NCT00894166. CHRNA5 genotypes are being used as a biomarker to prospectively stratify individuals in a ongoing RCT (NCT02351167) to evaluate moderation of treatment efficacy, adverse events and medication compliance. We nominate a more inclusive biomarker, total nicotine equivalents or TNE. TNE, comprised of nicotine, cotinine, trans-3'-hydroxycotinine, their glucuronides, and sometime nicotine N'-oxide, accounts for 90% of nicotine metabolites. The use of nicotine metabolites provides greater power for detecting genetic effects related to smoking behaviors due to the increased precision of the biomarker. Our pharmacogenomic prediction of TNE will represent the combined effects of metabolic and pharmacodynamic genes and will be useful for personalized smoking cessation treatment.

Innovation

Prediction of nicotine biomarkers and cessation are needed to develop a pharmacogenomic test for personalized cessation therapy. Only recently have cessation trials begun applying biomarkers prospectively; most biomarker research has been retrospective. We and our Key Personnel are involved in three prospective biomarker stratified RCTs: NCT00991081 provided personalized pharmacotherapy using the ANKK1 locus before randomizing behavioral therapies; NCT01314001 stratified by the NMR before randomizing pharmacotherapies; and NCT02351167 is stratifying participants by CHRNA5 before randomizing to pharmacotherapy. RCT NCT00991081 demonstrated clinical feasibility, but sample size limited power to detect moderation of efficacy by genotype. RCT NCT01314001 demonstrated differences in efficacy and adverse event rates between metabolism activity categories. RCT NCT02351167 has recruited about half its target number of participants and is ongoing. These trials are testing nicotine metabolism and dependence biomarkers for clinical utility in smoking cessation treatment. By developing comprehensive models of these biomarkers in large multiethnic samples (MEC), there is a unique opportunity to develop a comprehensive pharmacogenomic test with components that could be expedited into clinical use.

Figure 7:
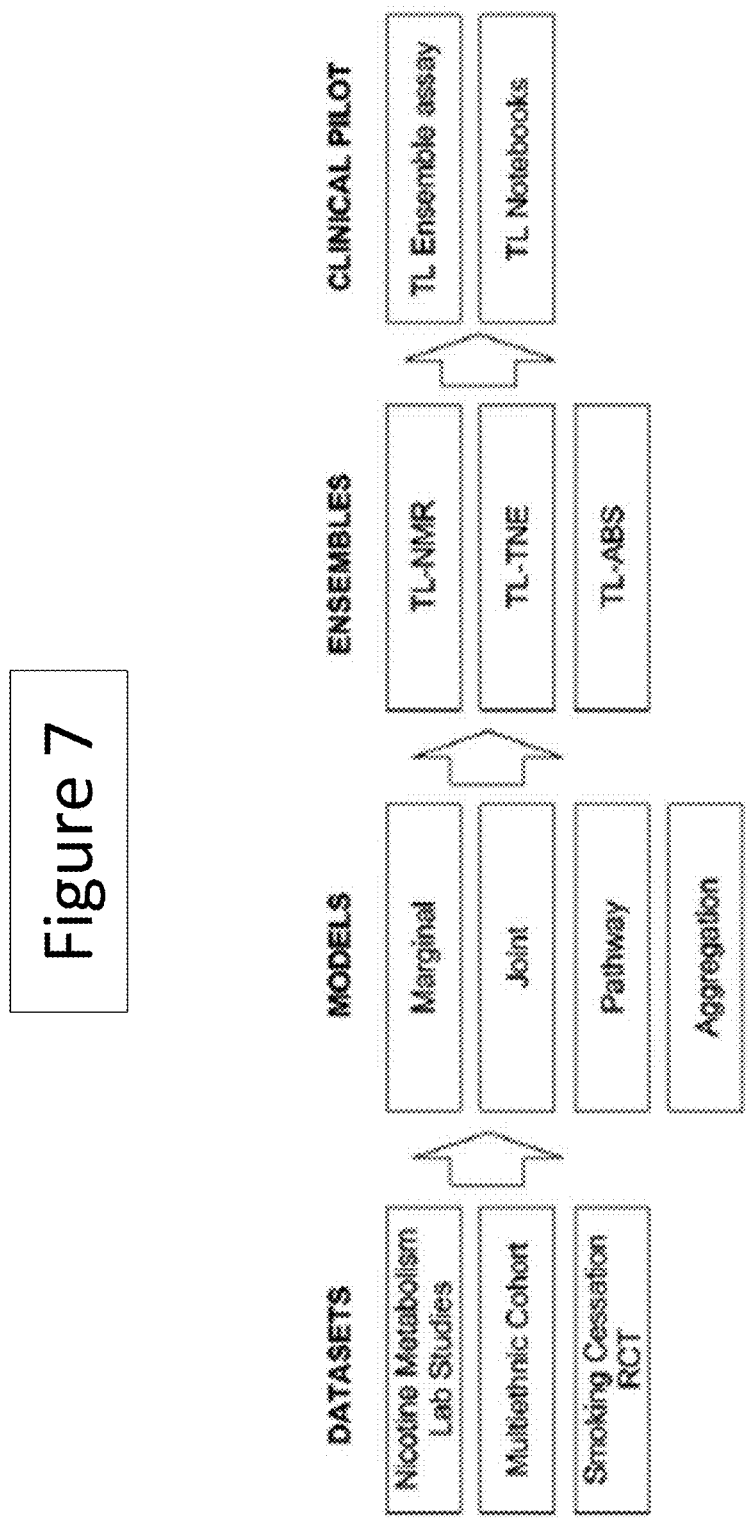
FIG. 7 shows an overview of the phase II approach to the present invention.
Figure 8:
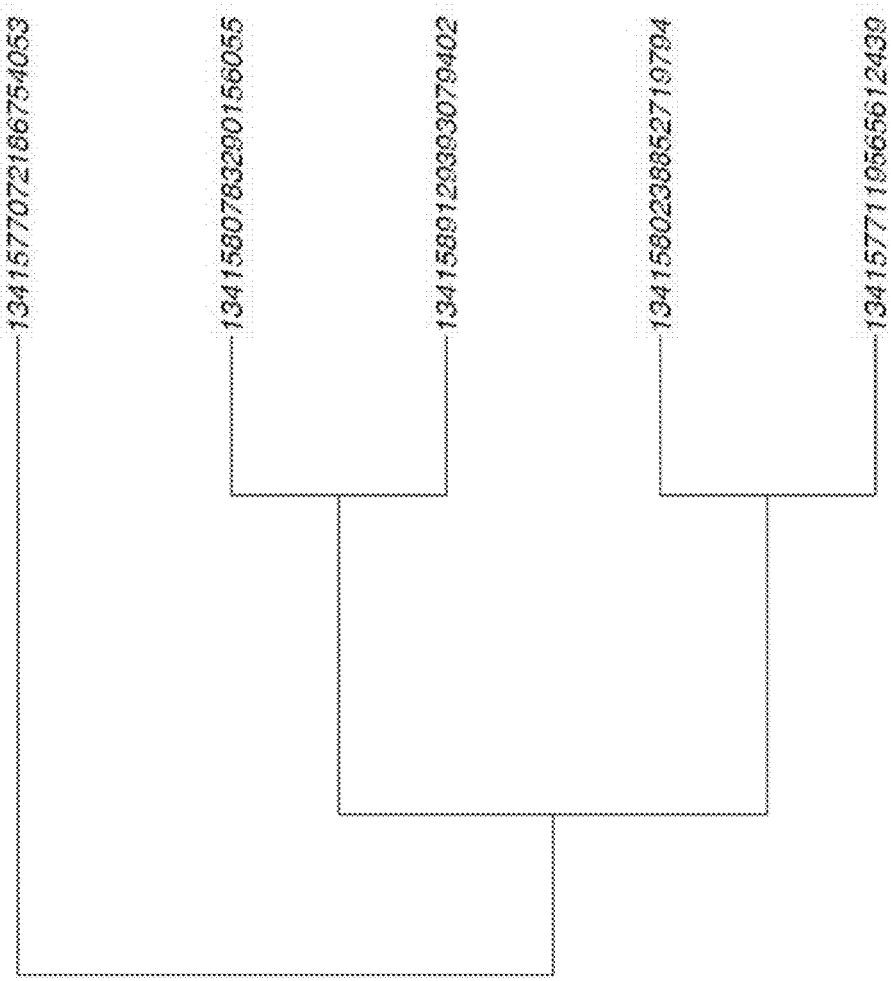
FIG. 8 shows a top tree with genetic variants.

In Phase I, we performed the largest genome-wide analysis of laboratory-based nicotine metabolism using innovative statistical learning models. In these laboratory studies (METS), participants were given fixed doses of labeled nicotine and metabolites were assessed over time. In Phase II, we propose analysis of nicotine metabolites in current smokers in the Multiethnic Cohort (MEC, N=2239, see FIG. 7). Uniquely, the MEC has clinical (smoking and drinking history, diet, current medications) and biomarker (the NMR and TNE) data and DNA from individuals representing five major American ethnicities. The MEC is large enough to characterize genomic differences in metabolic enzymes that influence ethnic differences in the NMR and TNE. We will relate nicotine pharmacogenomics to smoking cessation therapies in RCT NCT10553084 (N=1,086), identifying biosignatures predictive of NRT, C-NRT and VAR efficacy. This study is the only RCT comparing the two top smoking cessation therapies (C-NRT and VAR).

MEC and RCT DNA samples will be genotyped using a common platform (Smokescreen®GTA) that we have already designed and validated. This array has dense coverage of the CYP2A6 and CHRNA5 regions, and over 1,000 genes involved in nicotine metabolism, addiction, and attributable disease—more than any commercially available array. The data from this array will increase the power to identify biosignatures in these datasets. The RCT NCT10553084 is the first of several RCTs that will be genotyped using Smokescreen®GTA by NIDA.

Datasets

Laboratory Studies of Nicotine Metabolism (METs)

We previously selected unrelated African-American (N=52), Asian-American (N=55), and European-American (N=239) ancestry individuals from three METs for Smokescreen®GTA genotyping. Biospecimens were collected and nicotine metabolite levels assessed using mass-spec methods. For METS, the nicotine metabolite ratio (NMR) is defined as the 360 minute trans-3'-hydroxycotinine to cotinine ratio.

Pharmacokinetics in Twins ("PKTWIN"): Participants were recruited from the Northern California Twin Registry to investigate heritability components of nicotine metabolism. Participants consented to 30-minute venous administration of deuterium-labeled nicotine and cotinine, followed by an eight-hour hospital stay and blood and urine sample collections.

Pharmacogenetic Study of Nicotine Metabolism ("588"): Stratified recruitment for a nicotine and cotinine metabolism study of self-identified Asian, African and European American individuals by current smoking status and by sex through multi-media advertisements was performed. Participants consented to morning oral administration of labeled nicotine and cotinine. The following biospecimens were collected: saliva up to 60 hours after dosing; blood up to 480 minutes; and, urine up to 8 hours.

Smoking in Families ("SMOFAM"): Individuals from 61 pedigrees (with at least three ever-smokers individuals per pedigree and who were originally recruited to assess the relations between genetic factors, environmental factors, and tobacco use) completed a clinical study of nicotine metabolism. Monitored by a nurse at home, a fixed dose of labeled nicotine and cotinine was administered orally, salivary samples were collected at multiple time points.

Multiethnic Cohort, MEC

The MEC was established in Hawaii and in California to study diet and cancer in the United States. Individuals of both sexes, aged 45-75, and from five major ethnicities (Latino, African-American, Japanese-American, White, Native Hawaiian and other) were recruited using driver's license and voters' registration files, first name and surname lists from multiple sources, and Health Care Financing Administration lists. The investigators designed a recruitment strategy to include all socioeconomic strata within each ethnic group. A dietary questionnaire for food items for each ethnic group and major nutrients of interest was developed in a multi-step process; in addition, demographics, behavior, medical history, family cancer history, concomitant medications, and female reproductive history and use of exogenous hormone were included on the self-administered questionnaire. Nutrient values were weighted by frequencies of consumption supported by an ethnic specific food database; a calibration study was performed to estimate correlations of absolute intakes, nutrient densities and energy adjusted nutrients. Cohort ascertainment began in 1993 and was completed in 1996; cohort size is 215,251.

MEC Biospecimen Subgroup. A subgroup of the MEC were recruited by letter and then by phone, followed by a phone interview to update baseline information, recent smoking history and current medication use. Blood was drawn at participants' homes or at a clinical lab, and overnight (Hawaii) or first morning (California) urine was collected. The MEC Biospecimen Subgroup ascertainment began in 2001 and was completed in 2006; 67,594 participants contributed biospecimens.

MEC Current Smoker Biospecimen Subgroup. To create the MEC Current Smoker Biospecimen Subgroup (N=2,239), all current smokers in the MEC Biospecimen Subgroup who were cancer free were identified, and urine was analyzed using liquid chromatography-tandem mass spectrometry for nicotine (NIC), cotinine (COT), trans-3'-hydroxycotinine (3HC), total NIC, total COT, total 3HC (i.e., including glucuronidated metabolites), and nicotine N'-oxide (NNO) metabolites. CVs from 10 replicate determinations for NIC, COT and 3HC were 16.7%, 10.1% and 11.4%.

RCT NCT01553084

NCT01553084 was designed to compare efficacies of VAR, the most effective smoking cessation pharmacotherapy, C-NRT, sometimes ranked as the most effective pharmacotherapy, and NRT patch. Participants were recruited from two community cohorts drawn from two Midwestern cities. Inclusion criteria were current smoking of >4 cigarettes per day, age >17 years, ability to read and write English, desire to quit and to use smoking cessation therapies but not currently in treatment, agreement to not use e-cigarettes and to use birth control. Exclusion criteria included carbon monoxide (CO)<4 ppm, use of other forms of tobacco, and a group of chronic diseases or current treatments including renal, psychiatric, cardiovascular, cerebrovascular, and metabolic disorders. Participants were computer randomized, stratifying by site, sex, and race to VAR, C-NRT and NRT unblinded treatment in a 5:5:3 ratio. Smoking behavior and history, and psychiatric and physiological screenings were performed; treatment began one week before the target quit day, and included five in person counseling sessions and one telephone call totalling 80 minutes, while study medication was dispensed twice. Assessment of withdrawal, CO, adverse events and adherence were evaluated at the five treatment contacts and use of tobacco products was assessed at 26 and 52 weeks post-quit by phone. Self-reported abstinence was verified by CO.

Smokescreen®GTA Genotyping

The analysis in this project will use BioRealm's Smokescreen®GTA for unified genomic data. The platform was designed for genomic research on smoking behavior, addiction, pharmacological treatment, and related disease. Smokescreen®GTA includes 646,247 markers in 23 categories. The array design covers genome-wide common variation (66%, 82%, and 91% in African (YRI), East Asian (ASN), and European (EUR) respectively); most of the variation with a minor allele frequency≥0.01 in 1,014 addiction genes (85%, 90%, and 90% for YRI, ASN, and EUR respectively); and, nearly all variation in CHRNA5-CHRNA3-CHRNB4 and CYP2A6-CYP2B6 regions.

DNA samples from the METs have been previously genotyped with Smokescreen®GTA. RCT NCT01554084 has been genotyped with Smokescreen®GTA under the NIDA Genetics Consortium's genotyping initiative (see letters of support from Drs. Baker and Bierut). DNA samples from smokers in the Multiethnic Cohort will be genotyped on Smokescreen®GTA. Drs. Park and Le Marchand (see letters of support) will send extracted DNA samples to RUCDR Infinite Biologics for genotyping. Raw data from each project will be processed using BioRealm's QC, ancestry estimation, and imputation procedures. The more stringent QC procedures for genotyped and imputed variants developed in Phase I for CYP2A6 will be applied to the genomic regions targeted for analyses. All bioinformatic workflows will be maintained on BioRealm's GitLab server. Data will be stored on BioRealm's secure file server and project database maintained by Mr. Ryan.

Clinical data and collaborators METs data have been provided by Dr. Swan. MEC data will be provided by Dr. Park who will coordinate data extraction with MEC PIs. NCT10553084 data will be provided by Dr. Baker and Dr. Bierut. Data from smoker cohorts will be provided by Dr. Chen, Dr. David and Dr. Cullen.

Statistical Models

General

The relationship between each outcome Y (NMR, TNE, ABS) and the available explanatory variables will be assessed through an ensemble of high-dimensional regression techniques belonging to both the frequentist and Bayesian paradigms. The set of P explanatory variables for each participant consists of P1 confounding variables (e.g., age, ethnicity, gender, body mass index (BMI), etc.), P2 genomic variables (e.g., genotypes), and P3 derived variables (e.g., interactions and predicted biomarkers), where P=P1+P2+P3. Modeling will proceed under the assumption that the conditional mean of Yi, the response measured on the ith participant, depends on the explanatory variables through the link function g(•); i.e., $$g(\mu_i) = \beta_0 + \sum_{j=1}^{P_1} \beta_{1j} C_{ij} + \sum_{j=1}^{P_2} \beta_{2j} G_{ij} + \sum_{j=1}^{P_3} \beta_{3j} Z_{ij},$$

where $C_{ij}$, $G_{ij}$, and $Z_{ij}$ denote the jth confounding, genetic, and derived variables measured on the ith participant, respectively, $\mu_i$ denotes the conditional mean, and the $\beta_{kj}$ are regression coefficients. A key feature of these data are that the number of genomic variables (i.e., P2) and possibly the number of derived variables (i.e., P3) are substantially greater than N, thus traditional regression techniques will be inadequate for conducting a joint analysis. This particular issue will be addressed in two ways, that is through a marginal analysis and by employing penalized regression techniques, with the former being a staple among traditional GWAS while the latter represents a more advanced treatment that permits a full joint analysis.

Marginal As a means to evaluate the potential explanatory ability of genomic variables in an exploratory fashion, an initial marginal analysis will be conducted. This study will consider fitting and evaluating reduced models of the for $$g(\mu_i) = \beta_0 + \sum_{j=1}^{P_1} \beta_{1j} C_{ij} + \beta_{2j} G_{ij},$$

for j=1, . . . , P2. P-values for β2j will be computed in the usual fashion. Due to the highly correlated nature of genetic data, this approach will likely possess an extremely high false discovery rate, even after adjusting for multiple comparisons. Moreover, it is expected that this approach will fail to identify some significant genetic variables. This analysis will serve exploratory purposes only, and can potentially help identify key features of the data that need to be accounted for.

In Phase I, we applied a marginal analysis of the NMR in the METs. The marginal analysis highlighted that variants near CYP2A6 are important but not exclusive predictors of NMR. The EGLN2, CYP2A6, CYP2A7, CYP2G1P, CYP2B7P1, CYP2B6 complex had the strongest association pattern (See FIG. 2; black dots). Many associations in the region were significant due to the strong correlation between variants (linkage disequilibrium). A more comprehensive modeling approach was clearly needed.

Joint In order to develop predictive models, identify important genomic variables, and to correctly account for confounding effects, high-dimensional regression techniques will be utilized. This will be accomplished by assuming that the outcome Y conditionally, given the explanatory variables, follows a distribution belonging to the class of generalized linear models; i.e., follows a distribution whose probability density function is given by $$f(y \mid \theta, \phi) = \exp\left\{\frac{y\theta - b(\theta)}{\phi/w} + c(y, \phi)\right\},$$

where φ and θ are the dispersion and canonical parameters, respectively, w is a known weight, and b(•) and c(•, •) are known functions. In this framework, explanatory variables are related to the response in the usual fashion; i.e., μ=b 0 (θ). Here it is understood that θ is a function of the regression coefficients, which for ease of exposition are denoted as β; i.e., θ=θ(β). The penalized estimator is then obtained as the maximizer of $$Q(\beta) = l\{Y \mid \theta(\beta), \phi\} - \sum_{k=1}^{3} \sum_{j=1}^{P_k} p(\beta_{kj}, \lambda)$$

where l{Y|θ(β), φ} is the observed data likelihood of the N observations and p(•, •) is a penalty function, with λ being tuning parameters. Through the choice of the data model (i.e., f) and the penalty function, many common high-dimensional regression techniques can be framed under the approach described above; e.g., selecting p(βkj, λ)=λ|βkj| leads to the least absolute shrinkage and selection operator (LASSO); p(βkj, λ)=λ|βkj|/|βb kj| provides the adaptive LASSO estimator, where the βb kj are a priori estimates of βkj; the elastic-net is given when p(βkj, λ)=λ1|⊖kj|+λ2β 2 kj; and Bridge regression when p(βkj, λ)=λ|βkj|q, for q>0, with q=1 and q=2 reverting to ridge regression and LASSO, respectively. The salient point, the formulation provided above will permit the joint analysis under many common penalty structures, each of which are designed to provide gains with respect to estimation accuracy in the face of data issues such as multicollinearity, outlying observations, etc. Several additional techniques which will be utilized to conduct joint analyses include smoothly clipped absolute deviations, minimax concave penalty, SCAD-ridge, MCP-ridge, etc. Other high-dimensional regression techniques, which generally fall outside of the formulation provided above, that will be considered are the Dantzig Selector and the Lq-LASSO. The motivation behind this ensemble based approach to model fitting/selection is that we will in essence "leave no stone unturned." Of course, this beckons the question how will the results from these analyses be aggregated into a single predictive model?

This general formulation will support the joint analysis of the different outcomes of interest; e.g., it is expected that NMR and THE will (after appropriate transformations) be well modeled through the use of normal errors regression models, while binary regression models will be appropriate for Smoking Abstinence. If issues arise which invalidate the use of the aforementioned high-dimensional regression techniques, we plan to turn to the Bayesian paradigm. In particular, one will note that the formulation of Q(β) suggests that an analogous Bayesian analysis could be conducted, using independent priors for the regression coefficients which are of the form π(βkj)∝exp{−p(βkj, λ)}. In fact, recognizing this fact has led to the development of several shrinkage priors within the Bayesian paradigm; e.g., the Bayesian LASSO; the Bayesian elastic-net. Moreover, a vast cadre of shrinkage priors have been proposed; for examples and further discussion. Using these shrinkage priors, the model fitting/selection goals described above could be accomplished through deriving the maximum a posteriori estimator.

Figure 3:
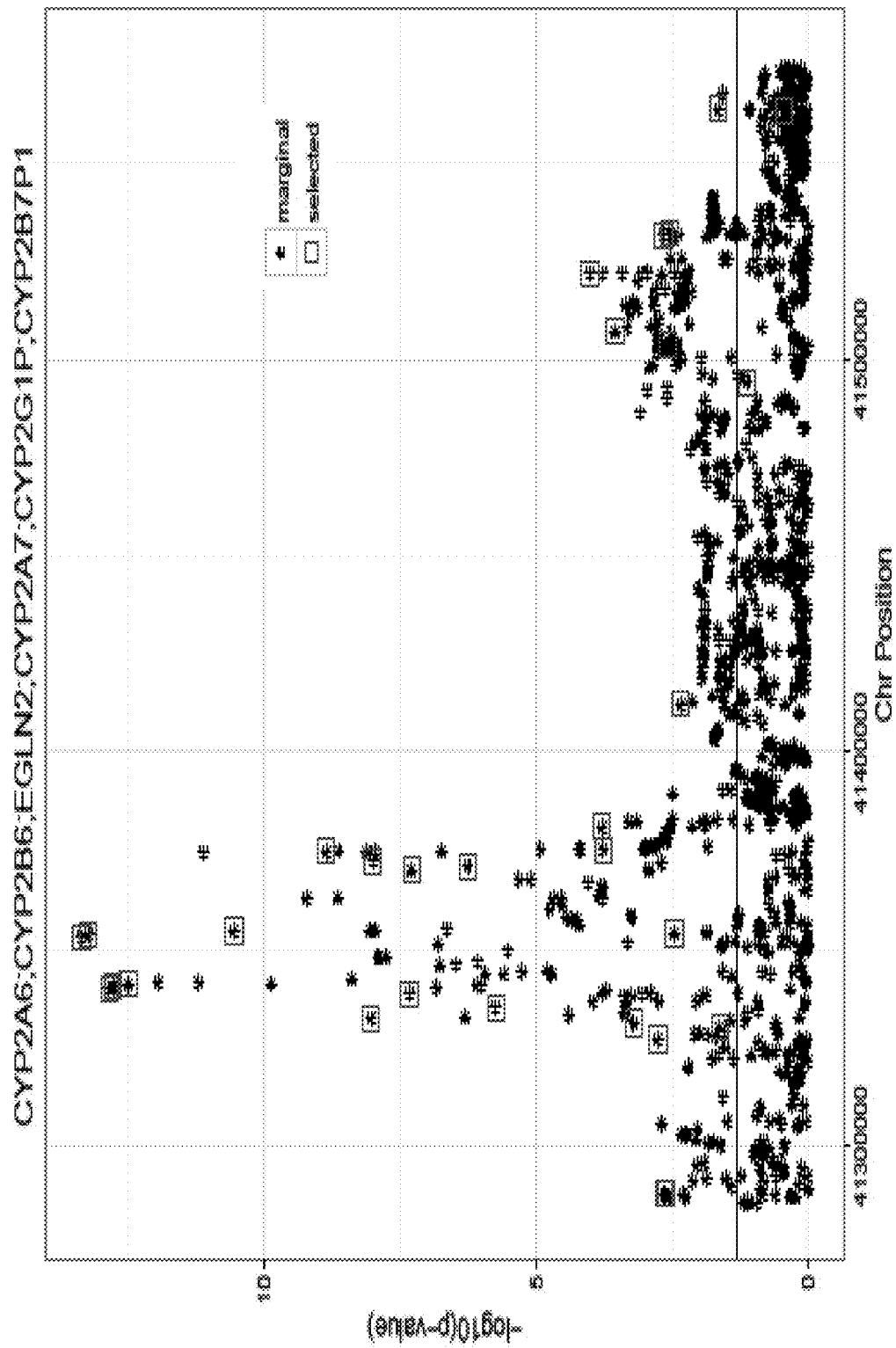
FIG. 3 shows genetic associations with nicotine metabolism in the CYP2A6 Region of Human Chromosome 19.

In Phase I, we applied many of these joint modeling techniques to the NMR dataset. In the ensemble of 14 statistical learning models, five SNPs (out of 3752 SNPs) were selected in all models as significant predictors of NMR (FIG. 3). These predictors (selected in the lq-LASSO q=1.00 model) explained 37% of NMR variation. The Adaptive-LASSO selected one additional SNP, was the best model by AIC and BIC and accounted for 43% of NMR. The largest model SCAD-Ridge(alpha=0.18) had 63 SNPs. More parsimonious models explained NMR just as well with fewer SNPs (58-62% NMR). Note however, in some embodiments the present invention may use at least two statistical learning models in an ensemble. In some embodiments the present invention may use 2-14 statistical learning models in an ensemble. Also, the present invention may use more than 14 statistical learning models in a single ensemble.

The significant SNPs found in the EGLN2, CYP2A6, CYP2A7, CYP2G1P, CYP2B7P1, CYP2B6 complex by penalized regression approaches are overlayed on the marginal results in FIG. 2. The model ensemble clarifies the independent signals near the CYP2A6 and CYP2B6 genes. Models within the ensemble have different properties and therefore flag different features in the data. Using model diversity to enhance prediction will be a hallmark of our Phase II analytic strategy.

Pathways We propose using Bayesian approaches to build prediction models of complex relationships among genetic variants influencing NMR, TNE, and ABS. These approaches may improve prediction by accounting for model uncertainty, representing the underlying biology driving associations, and leveraging existing pathway knowledge.

Here we include a derived "pathway" variable ZΛ in the general regression framework outlined above, with a corresponding coefficient βΛ representing the net effect of multiple genetic factors. The pathway variable is computed using a system of equations: ZΛ=θ1W1+θ2W2+(1−θ1−θ2)W1W2

A range of interactions can be represented through the set of parameters θ. For example, if θ1=θ2=0, only the combination of both variables yield an effect, akin to a logical if W1 and W2 were binary. These equations can be stacked as a binary tree, such that ZΛ is the root and its children W1 and W2 can either be observed genetic variables (a leaf) or other similarly derived variables (internal nodes).

The posterior of these tree structures can be expressed as $$p(\Lambda \mid \mathcal{D}) = \frac{p(\mathcal{D} \mid \Lambda) p(\Lambda)}{\sum_\Lambda p(\mathcal{D} \mid \Lambda) p(\Lambda)}$$

where D is the data, p(D|Λ) is the marginal likelihood, and p(Λ) is the tree prior. Depending on the number of candidate variables and the complexity of the trees considered, one can either compute p(Λ|D) directly (by visiting all possible trees) or by approximation via Markov-Chain Monte Carlo (MCMC) methods. Rather than integrating over the tree parameters to obtain the marginal likelihood for a given tree, we use the BIC approximation based on its maximum likelihood p(D|^θ, β^Λ). The tree prior p(Λ) is based on its distance to a "forest" capturing known relationships among genes in relevant biological pathways as a collection of binary trees.

We propose a staged approach for fitting these pathway models. First, we'll perform local searches by visiting all (P2) trees and computing the marginal posterior probabilities for the genetic variables in the set. Secondly, we will use this information to initialize and streamline a MCMC algorithm exploring more complicated combinations of genetic variables. The MCMC algorithm will be initialized to the best 2-input tree. Information will be propagated from the previous local searches to propose intelligent moves through the model space (by adding, removing, and replacing variables in the tree). The findings will be sorted by evidence using Bayes factors (the ratio of posterior to prior odds). The posterior probabilities, net pathway effects βA, and BIC, AIC, and R2 metrics will be summarized.

Figure 4:
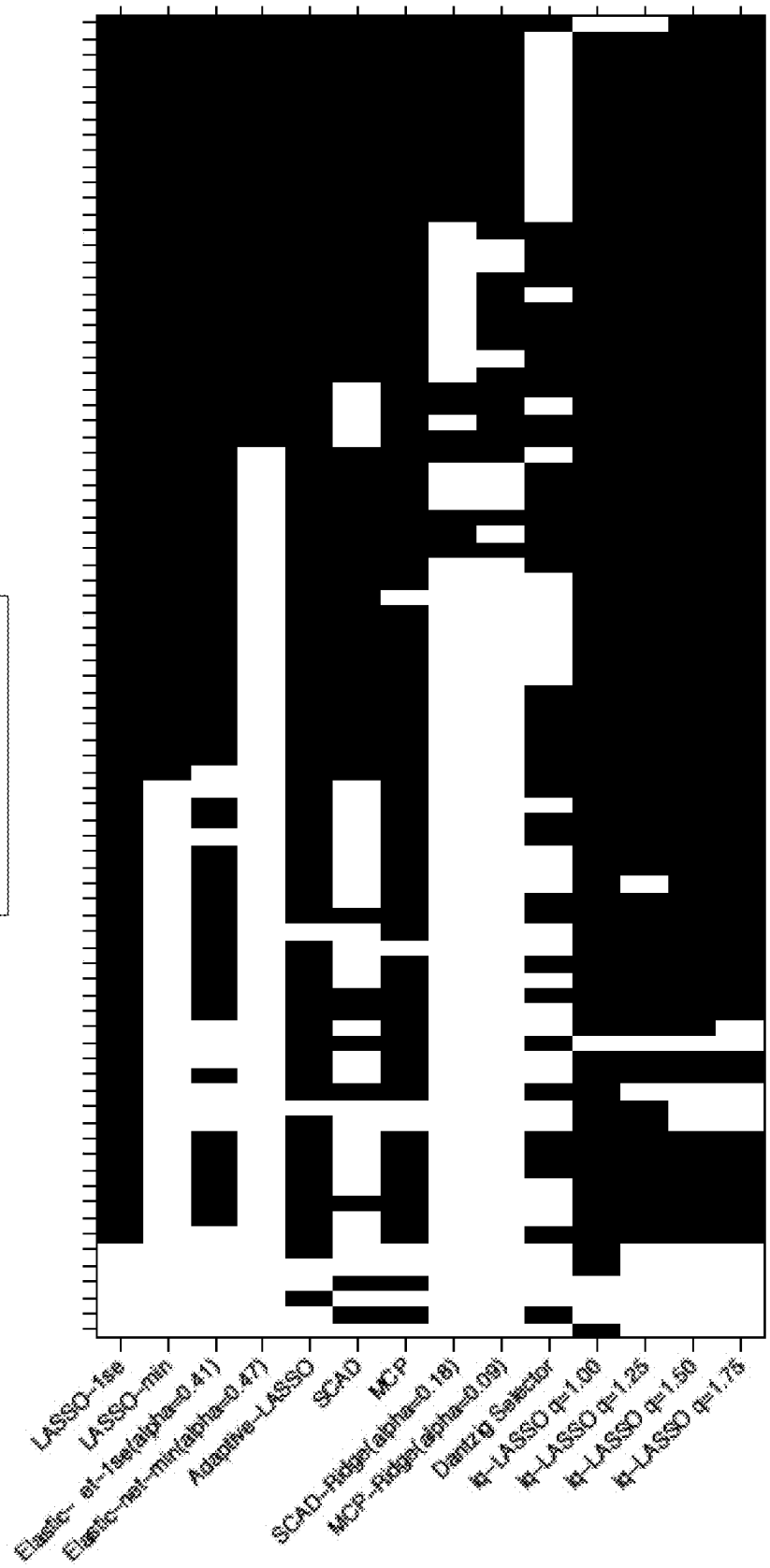
FIG. 4 shows an ensemble of models to define biosignatures.

We performed a proof-of-principle pathway analysis of NMR in Phase I. We considered >7 million trees comprised of variants within nicotine metabolism genes. We discovered that rs56113850 (in CYP2A6) was an important hub, with other SNPs added to or modifying its effect on NMR (FIG. 4). The pair rs56113850 and rs143711947 (both in the CYP2A6 region) was highly associated with NMR (Bayes Factor=2.1E6). Variants within HNF4A, NFE2L2, NR1I3, POR, UGT1A4/A9, and UGT2B10 also had strong evidence of interactions with variants in the CYP2A6 region (Bayes Factors>6.3E3).

We continued our Phase I analysis by demonstrating feasibility for a larger pathway search. Using the variants with the highest posterior probabilities from the previous step, we searched for more complicating interactions using MCMC. The tree comprised of rs56113850 and rs143711947 had a posterior probability of 0.2% and jointly reduced NMR (βΛ=−0.58). Trees with higher posterior probabilities contained 4-6 SNPs and had strikingly similar measures of fit (e.g, AIC, BIC, R2). The top tree contained 5 genetic variants and had a posterior probability of 0.9%. The net effect of this pathway on NMR was βΛ=−1.35) and explains 43% of the NMR variance. This preliminary analysis highlighted that multiple pathway models fits the data well and there are combinations of variants that together have large impacts on NMR (e.g., four SNPs yielded a βΛ=−2.42).

Other Approaches

Should linear modeling assumptions not be met, we will apply non-linear machine learning (ML) approaches. Machine learning offers a number of unique regression and classification algorithms that predict new observations based on previous experience. These have been shown to excel in prediction for many medical applications, but suffer due to confounding in others. In the statistical methods proposed, the significance and effects of the explanatory variables are estimated while accounting for confounding (e.g., population stratification). Thus inference and consequentially predictions have epidemiological context. These variable selection and interpretation requirements would be difficult to incorporate into many non-linear ML algorithms. However, there is active development of extending ML methods to address some of these issues. We will evaluate such implementations (e.g, mixed random forest, generalized multifactor dimensionality reduction (MDR), deep convolutional neural networks should problems arise in the primary analytic strategy.

Prediction Ensemble

Fundamentally, the problem of identifying the "best" model, whether using advanced or traditional regression techniques, has plagued statisticians for ages. That is to say, in many cases analysts tend to select a "best" model from a set of candidate models, based on a predetermined model selection criteria (AIC, BIC, CV, etc.), and proceed (with further analyses, inference, and prediction of future outcomes) as if the selected model were the truth ignoring the uncertainty in the model selection procedure. This process, due to the uncertainty introduced through model selection, may lead to making over-confident predictions, inference, and ultimately decisions. To the point, prediction performance relies on successfully accounting for uncertainty in the model inputs (e.g, measurements), model parameters, and the model itself. For this reason, we propose to develop and implement a prediction "ensemble" consisting of the models outlined in the previous sections. An ensemble is a collection of models whose predictions are combined by weighted averaging or voting.

Unlike traditional techniques, some embodiments of this invention, all of the models are combine into a single predictive model, thus leveraging the predictive capacity of each independent model. To acknowledge the fidelity of the models, weighted averaging, for example, may be employed. That is, in some embodiments, this invention adaptively gives more weight to the models that are better predictors. This may be accomplished using k-fold cross-validation being as a metric that may be used to assess prediction. In the context of a nicotine metabolite ratio model ensemble there may be, for example, 14 models that predict NMR from different genetic and clinical variables. Each model may have an initial weight, but as the ensemble is applied to data, better performing models may be upweighted and poorer models are down-weighted.

In some embodiments, voting techniques may be used in a similar manner to the averaging techniques described above with the salient difference that the developed models are for qualitative data. Given the nature of the data that may be used, each predictive model may be thought of as a "voter" and by taking the weighted average over each of these voters, predictions may be able to get more of a robust prediction of qualitative outcomes.

Dietterich (2000) states that "A necessary and sufficient condition for an ensemble of classifiers to be more accurate than any of its individual members is if the classifiers are accurate and diverse." Further, "model diversity" improves prediction because different models captures different signals in the data. The goal of designing the ensemble based predictive model will be to borrow across the strength of multiple models and guard against their weaknesses.

Aggregation Methods

For ease of exposition, from hence forward the discussion will be centered around a normal errors regression context, with extension to other data structures following a similar logical development. The first technique, which will be investigated, is referred to as stacked regression, and it proceeds as follows. Let fm, for m=1, . . . , M denote the model fit obtained through one of the aforementioned regression procedures. In stacked regression, each of these fitted models are treated as a new predictor and a new model (which can be thought of as a weighted average of the original models) is proposed as $\Sigma M\ m=1\ \alpha_m\ f_m$, where $\alpha_m$ can be thought of as weights. Using the observed response variables, the $\alpha_m$ can be estimated via ordinary least squares (OLS), or as the minimizers of some other metric (e.g., BIC, AIC, R2, etc.). Obviously, there will exist a high degree of multicollinearity between the fm, thus relying solely on OLS estimation may not be reliable for estimating the am, in which case we will employ techniques designed to perform well in the presence of multicollinearity; e.g., ridge regression or the leave-one-out cross validation proposal of Breiman et al. Other methods of developing an ensemble model that will be considered include bootstrap aggregating, boosting, ensemble selection from libraries of models, and Bayes model averaging.

Prediction Performance

The different model construction strategies will lead to an ensemble for each outcome. A in-depth ensemble validation process will be employed. First, apparent validation, which seeks to assess the performance of the model on the data used to develop it, will be conducted via standard techniques; e.g., cross validation, AIC, BIC, R2, confusion matrix, rank models, receiver operating characteristic (ROC) curve analysis etc. Second, internal validation, which aims at validating models for the population underlying the sample of the particular study, will be conducted via bootstrapping techniques. Lastly, external model validation will be conducted as new data from additional studies becomes available.

TABLE 1

Variables for NMR, TNE, and Smoking Abstinence Modeling

| Matrix | Domain | Details | Ensemble |
|---|---|---|---|
| G | Nicotine metabolism | See 4.2.1 | TL-NMR, TL-ABS |
| G | Nicotine | See 4.2.2 | TL-TNE, |

TABLE 1-continued

Variables for NMR, TNE, and Smoking Abstinence Modeling

| Matrix | Domain | Details | Ensemble |
|---|---|---|---|
| | dependence | | TL-ABS |
| G | Smoking cessation | See 4.2.3 | TL-ABS |
| C | Treatment | NRT, C-NRT, VAR | TL-ABS |
| C | Demographics | site, age, sex, race, BMI, smoking, status, current drinking | TL-NMR, TL-TNE, TL-ABS |
| C | Cessation demographics | education, income, carbon monoxide level, home smoking, prior cessation medication use, menthol cigarette use | TL-ABS |
| C | Behavior scores | FTND total score, TIPC, self-reported likelihood of quitting | TL-ABS |
| Z | Predicted biomarkers | $Z_{NMR}, Z_{TNE}$ | TL-ABS |
| Z | Biomarker-treatment | $Z_{NMR}C_T, Z_{TNE}C_T$ | TL-ABS |
| Z | Pathways | $Z_A$ | TL-NMR, TL-TNE, TL-ABS |

SmokescreenTL Ensemble

Development Prediction ensembles will be developed for nicotine biomarkers and smoking abstinence. Drs. Mcmahan and Conti will advise on statistical modeling issues (see letters of support). The TL-NMR and TL-TNE ensembles will include models of the nicotine metabolite ratio (NMR) and total nicotine equivalents (TNE) discovered and validated in the METs and the MEC (see FIG. 7). An alternative ensemble (TL-NMRcat) will be considered with NMR categorized into slow or normal metabolism based on thresholds used in recent RCTs. The TL-ABS ensemble will include models of smoking abstinence (ABS) discovered in the RCT NCT01553084 dataset. The explanatory variables considered in building each ensemble are described in Table 1. Before analysis begins, we will consult with our scientific and clinical advisers to update the variables and generate pathway modeling priors. For TL-ABS, treatments will be included with indicator variables indicating C-NRT and VAR with NRT as a reference. Note that predictions of the nicotine biomarkers ZNMR and ZTNE will be considered as derived variables in the modeling of ABS. It is important to note that additional variables may be considered in future ensembles as additional studies become available.

Smokescreen®TL Implementation and Clinical Pilot

The genomic biosignature of the TL-NMR, TL-TNE, and TL-ABS ensembles will be implemented into a costeffective, high quality, and high-throughput genotyping technology, suitable for deployment in CLIA environments. A data management and analysis workflow will be implemented on BioRealm's secure servers to (1) process incoming genotyping data, (2) combine it with incoming clinical data in a database, (3) create an analytic dataset, (4) predict NMR, TNE, and ABS by applying the current ensembles (clinical, genotype, and derived variables; parameter and model weights within an ensemble), and (5) create a notebook for delivering results to the user. This will be implemented in Python, and PostgreSQL. The resulting system will be demonstrated in clinical pilots of smokers recruited from treatment programs at Washington University and Stanford University (see letters of support).

Smokescreen®TL Ensemble Array A custom, high-throughput SNP genotyping array using Fluidigm microfluidic dynamic array technology will be developed with RUCDR Infinite Biologics for rapid clinical screening of 24

DNA samples at a time. RUCDR has developing, validated, and is using this technology in their own RUIDTM array used for screening hundreds of thousands of bio-bank samples. We will select 192 markers to capture the relevant NMR, TNE, and ABS biosignatures and additional high-value targets. The following modules will be considered in the design: (1) American Ancestry Informative Markers (AIMS, m=22) for distinguishing African, Caucasian, East Asian, and Hispanic Americans; (2) SNPs within the TLNMR, TL-TNE, and TL-ABS ensembles; (3) clinically significant markers, including CYP2A6 copy number and rs56113850, chr15q25.1 haplotypes (m=2), and markers for guiding choice of smoking cessation selected by the Cochrane protocol (m=13).

Should the prediction ensembles require more than the number of targets that can be included on one array, we will first attempt to prune the ensemble based on prediction performance. If all the content is needed, we will consult with Drs. Brooks and Tischfield on alternative strategies (e.g., separate arrays for each ensemble). Targets not performing well on the array or in the ensemble models may be replaced in future versions of Smokescreen®TL.

Smokescreen®TL Notebooks We acknowledge that organizations will have their own preferred result delivery mediums and channels. SmokescreenTL®Notebooks will be the flexible, reproducible, and secure reporting interface to the end user. Results will be presented concisely, securely, and understandably via different delivery channels (e.g., email, dynamic websites, printed materials, and even Git repositories).

Within a SmokescreenTL®Notebook a user will be able to view the input data, key clinical variables and genotypes, predicted ancestry, information about the prediction ensembles (version, methodology, performance), and the predicted nicotine biomarkers and smoking abstinence under different therapies. These reports can be presented for one smoker or aggregated across many.

SmokescreenTL®Notebook will be developed in Jupyter (http://jupyter.org/). Jupyter is open source, supporting over 40 programming languages and thousands of libraries that can be combined via pipelines into dynamic and interactive workflows. By combining Jupyter's powerful export features with traditional Linux scheduling mechanisms, reports can automatically be produced and made available automatically as needed via different delivery channels. In addition, another companion project, JupyterHub, can be incorporated into our technology stack to securely share TL Notebook to groups of users (https://github.com/jupyterhub/jupyterhub). SmokescreenTL®Notebooks will be developed and prototyped with our clinical collaborators.

Clinical Validation and Pilot RUCDR Infinite Biologics, as a CLIA laboratory and provider of clinical genomic services, will validate the array and workflows for clinical use. RUCDR will provide a detailed protocol and report of reproducibility, accuracy, and sensitivity of the Smokescreen®TL Ensemble Array.

Smokescreen®TL will be piloted on N=96 smokers involved in treatment at Stanford University (high risk smokers undergoing lung cancer screening and offered smoking cessation) and Washington University (community based treatment trial of smoking cessation). Patients will be recruited into research protocols that include Smokescreen®TL designed in collaboration with Dr. David and Dr. Chen (see letters of support). De-identified clinical and sample data will be provided to BioRealm. DNA samples (blood, preserved saliva or extracted DNA) will be sent to RUCDR Infinite Biologics. RUCDR will extract DNA and process the DNA samples on the Smokescreen®TL Ensemble Array and deliver the data to BioRealm. BioRealm will apply quality control and the TL-NMR, TL-TNE, TL-ABS ensembles to the data. Ancestry, select genotypes, and the predicted NMR, TNE, and smoking cessation probabilities by treatment will be returned to the clinicians for interpretation. The results will be presented in Smokescreen®TL Notebooks. We will iteratively provide prototypes of Smokescreen®TL Notebooks to our clinical collaborators at least twice to revise requirements. We will ask that our collaborators provide the smoking status of the patient during and post-treatment. These updates will be stored in a database and used to compute out-of-sample model performance metrics and update the ensemble weights over time. The pilots are intended to provide preliminary data prior to evaluating the Smokescreen®TL's clinical utility in larger cohorts or trials. These use cases will help streamline the Smokescreen®Ensemble Array, the ensembles, reporting, processes, and protocols.

In order to develop predictive models, identify important genomic variables, and to correctly account for confounding effects, high-dimensional regression techniques were applied to the laboratory studies of nicotine metabolism (METs). Explanatory variables considered included genetic variants in the nicotine metabolism pathway (Table 1), as well as clinical factors. In the following sections, we present the significant results from Phase I using marginal, joint, and pathway themed analytics.

TABLE 1

Genomic Regions in Nicotine Metabolism Modeling

| Gene Region | Protien Function | Chr | Region | SNPs |
|---|---|---|---|---|
| NR1I3 | steroid/xenobiotic receptor | 1 | 48,544 | 123 |
| FMO3 | monooxygenase | 1 | 66,941 | 329 |
| NFE2L2 | response to oxidative stress | 2 | 74,828 | 113 |
| AOX1 | oxidoreductase activity | 2 | 125,486 | 201 |
| UGT1A4 ... UGT1A9 | glycosyltransferase | 2 | 141,407 | 621 |
| UGT2B17 | glycosyltransferase | 4 | 71,342 | 15 |
| UGT2B10 | glycosyltransferase | 4 | 56,028 | 224 |
| UGT2B7 | glycosyltransferase | 4 | 56,512 | 262 |
| POR | cytochrome-b5 reductase | 7 | 111,753 | 243 |
| EGLN2.CYP2B6 | hypoxia response; drug metabolism | 19 | 289,524 | 1242 |
| HNF4A | hepatic transcription regulator | 20 | 117,044 | 379 |

Marginal Analysis

As a means to evaluate the potential explanatory ability of genomic variables in an exploratory fashion, an initial marginal analysis was conducted. The marginal analysis highlighted that variants near CYP2A6 are important but not exclusive predictors of NMR. The EGLN2, CYP2A6, CYP2A7, CYP2G1P, CYP2B7P1, CYP2B6 complex had the strongest association pattern (FIG. 3; black dots). Many associations in the region were significant due to the strong correlation between variants (linkage disequilibrium). A more comprehensive modeling approach was clearly needed.

Joint Analysis

We then created a model ensemble by generating joint models under many common penalty structures, each of which are designed to provide gains with respect to estimation accuracy in the face of data issues such as multicollinearity, outlying observations, etc. All models incorporated age and sex, while self-identified race and BMI were incorporated in models with 40 SNPs, respectively. In the ensemble of 14 methods, five SNPs (out of 3752 SNPs) were selected in all models as significant predictors of NMR (FIG. 2). These predictors (selected in the lq-LASSO q=1.00 model) explained 37% of NMR variation. The Adaptive-LASSO selected one additional SNP, was the best model by AIC and BIC and accounted for 43% of NMR (Table 2). The largest model SCAD-Ridge(alpha=0.18) had 63 SNPs. More parsimonious models explained NMR just as well with fewer SNPs (58-62% NMR).

The significant SNPs found in the EGLN2, CYP2A6, CYP2A7, CYP2G1P, CYP2B7P1, CYP2B6 complex by penalized regression approaches are overlayed on the marginal results in FIG. 3. The model ensemble clarifies the independent signals near the CYP2A6 and CYP2B6 genes. Models within the ensemble have different properties and therefore flag different features in the data.

In some embodiments of the invention, for validation of the biomarkers that are produced in the ensembles, cross validation may be used to reduce overfitting, for example, k-fold cross validation may be used. The dataset may be repeatedly partitioned k times, where a portion is used for training and another portion is used for testing. The results across repetitions are summarized allowing the entire dataset to be used. The ensemble of models may address underfitting. For example, you are more likely to capture different features of data using a collection of models because each model makes different assumptions about the data. In some embodiments the invention may use datasets with diverse samples (for example in some embodiments such as nicotine metabolism the invention may use samples that have different genetic ancestry Americans (European, Asian, African). These may improve the generalizability of the model, i.e. how the model does outside the initial samples. To evaluate generalizability of the model, we may examine the performance in independent datasets. Performance may be assessed, for example, by summarizing the differences between the prediction and the actual value for these new samples.

TABLE 2

Joint Regression Model Results

| Regression Method | SNPs | AIC | BIC | $r_p^2$ | $r_s^2$ |
|---|---|---|---|---|---|
| Adaptive-LASSO | 6 | 383.27 | 416.95 | 0.363 | 0.427 |
| MCP | 8 | 384.19 | 425.36 | 0.369 | 0.452 |
| LASSO-min | 41 | 389.89 | 558.33 | 0.483 | 0.599 |
| SCAD | 31 | 394.82 | 525.82 | 0.440 | 0.579 |
| lq-LASSO q = 1.75 | 11 | 410.57 | 466.72 | 0.331 | 0.444 |
| lq-LASSO q = 1.50 | 10 | 413.81 | 466.22 | 0.319 | 0.441 |
| lq-LASSO q = 1.25 | 10 | 415.41 | 464.07 | 0.312 | 0.427 |
| Elastic-net-min(alpha = 0.47) | 56 | 417.73 | 642.31 | 0.487 | 0.616 |
| LASSO-1se | 8 | 418.66 | 463.57 | 0.300 | 0.417 |
| lq-LASSO q = 1.00 | 5 | 425.57 | 455.51 | 0.266 | 0.369 |
| MCP-Ridge(alpha = 0.09) | 56 | 428.55 | 653.13 | 0.469 | 0.610 |
| Elastic-net-1se(alpha = 0.41) | 16 | 428.84 | 503.70 | 0.313 | 0.468 |
| Dantzig Selector | 43 | 436.52 | 616.19 | 0.411 | 0.577 |
| SCAD-Ridge(alpha = 0.18) | 63 | 448.73 | 699.51 | 0.458 | 0.609 |

Pathway Analysis

We used Bayesian approaches to build prediction models of complex relationships among genetic variants influencing the NMR. We used a staged approach for fitting pathway models, using tree structures to represent models.

First, we performed local searches on >7 million trees comprised of variants within nicotine metabolism genes (Table 1). We discovered that rs56113850 in CYP2A6 was an important hub, with other SNPs adding to or modifying its effect on the NMR (FIG. 3). The pair rs56113850 and rs143711947, both in the CYP2A6 region, were highly associated with the NMR (Bayes Factor=2.1E6; Table 3). Variants within HNF4A, NFE2L2, NR1I3, POR, UGT1A4/A9, and UGT2B10 also had strong evidence of interactions with variants in the CYP2A6 region (Bayes Factors>6.3E3). Associations with the NMR or its components have been described for CYP2A6, UTG1A4/A9, UGT2B10, POR, or their protein products; genetic associations of NR1I3, NFE2L2 and HNF4A and the NMR or its components have not been previously described.

Secondly, we used this information to initialize and streamline a MCMC algorithm exploring more complicated combinations of genetic variants. The MCMC algorithm was initialized to the best pairwise tree. The posterior probabilities, net pathway effects $\beta\Lambda$, and BIC, AIC, and R2 metrics were summarized.

The tree comprised of rs56113850 and rs143711947 had a posterior probability of 0.2% and jointly reduced NMR ($\beta\Lambda$=−0.58; Table 4). Trees with higher posterior probabilities contained 4-6 SNPs and had strikingly similar measures of fit (e.g, AIC, BIC, R2). The top tree contained 5 genetic variants (FIG. 4), and had a posterior probability of 0.9%. The net effect of this pathway on NMR was $\beta\Lambda$=−1.35) and explains 43% of the NMR variance. This preliminary analysis highlighted that multiple pathway models fit the data well and there are combinations of variants that together have large impacts on NMR (e.g., four SNPs yielded a $\beta\Lambda$=−2.42).

TABLE 3

Top Pairwise Interaction Model Results, by Bayes Factor

| SNP 1 | SNP 2 | Gene(s) | $\beta_\Lambda$ | p($\Lambda$|D) | Bayes Factor |
|---|---|---|---|---|---|
| rs56113850 | rs143711947 | CYP2A6 (IVS4, inter) | −0.67 | 0.2591 | 2.1E6 |
| rs56113850 | rs6508949 | CYP2A6 (IVS4, inter) | −0.50 | 0.1225 | 8.6E5 |
| rs2388868 | rs143711947 | CYP2A6 (IVS4, inter) | −0.68 | 0.0269 | 1.7E5 |
| rs56113850 | rs71334948 | CYP2A6 (IVS4, inter) | −0.36 | 0.0238 | 1.5E5 |
| rs56113850 | rs7247903 | CYP2A6 (IVS4, inter) | −0.57 | 0.0116 | 7.2E4 |
| rs56113850 | rs6031593 | CYP2A6, HNF4A | −0.25 | 0.0093 | 5.7E4 |
| rs56113850 | rs1645695 | CYP2A6 (IVS4, inter) | −0.59 | 0.0073 | 4.4E4 |
| rs79470484 | rs56113850 | POR, CYP2A6 | −0.49 | 0.0067 | 4.1E4 |
| rs77726520 | rs56113850 | POR, CYP2A6 | −0.49 | 0.0066 | 4.1E4 |
| rs10797094 | rs56113850 | NR1I3, CYP2A6 | −0.24 | 0.0064 | 3.9E4 |

TABLE 4

Phase I Pathway Models

| nSNP | p($\Lambda$|D) | $\beta_\Lambda$ | logLik | AIC | BIC | R2 |
|---|---|---|---|---|---|---|
| 5 | 0.009 | −1.35 | −232 | 378 | 453 | 0.43 |
| 4 | 0.007 | −1.72 | −227 | 380 | 448 | 0.42 |
| 5 | 0.007 | −0.84 | −232 | 378 | 453 | 0.43 |
| 5 | 0.007 | −1.29 | −232 | 378 | 453 | 0.43 |
| 4 | 0.005 | −2.33 | −228 | 382 | 449 | 0.42 |
| 4 | 0.004 | −2.06 | −226 | 378 | 446 | 0.42 |
| 4 | 0.003 | −0.39 | −232 | 390 | 457 | 0.40 |
| 4 | 0.003 | −2.17 | −227 | 381 | 448 | 0.42 |
| 4 | 0.003 | −2.27 | −227 | 379 | 447 | 0.42 |

TABLE 4-continued

Phase I Pathway Models

| nSNP | p(A|D) | $\beta_A$ | logLik | AIC | BIC | R2 |
|---|---|---|---|---|---|---|
| 6 | 0.003 | −1.63 | −233 | 370 | 453 | 0.45 |
| 4 | 0.003 | −0.54 | −229 | 384 | 451 | 0.41 |
| 4 | 0.003 | −0.59 | −229 | 384 | 452 | 0.41 |
| 5 | 0.003 | −0.81 | −230 | 375 | 450 | 0.43 |
| 6 | 0.003 | −1.15 | −233 | 369 | 452 | 0.45 |
| 6 | 0.002 | −0.81 | −234 | 370 | 453 | 0.45 |
| 5 | 0.002 | −1.09 | −234 | 382 | 457 | 0.42 |
| 4 | 0.002 | −2.42 | −227 | 381 | 448 | 0.42 |
| 5 | 0.002 | −1.29 | −231 | 376 | 451 | 0.43 |
| 4 | 0.002 | −2.23 | −227 | 380 | 447 | 0.42 |
| 2 | 0.002 | −0.58 | −224 | 396 | 449 | 0.37 |

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention not be limited by this detailed description, but by the claims and the equivalents to the claims appended hereto.

What is claimed is:

1. A computer-implemented method for biomarker discovery for predicting nicotine metabolism in a new subject, comprising:
   a. receiving high dimensional data containing, wherein receiving high dimensional data comprises collecting DNA samples from study subjects, genotyping the DNA samples collected, storing and processing data from the genotyped DNA samples collected on a server, and collecting individual characteristics of the study subjects on the server;
   b. measuring a nicotine metabolite ratio from each study subject and recording the measured nicotine metabolite ratio for each study subject on the server;
   c. training a machine to learn to predict an unknown nicotine metabolite ratio of the new subject by executing an ensemble of statistical learning models using the high dimensional data and measured nicotine metabolite ratios of each study subject, wherein the statistical learning models are selected from the group consisting of least absolute shrinkage and selection operator, ridge estimator, elastic net, adaptive least absolute shrinkage and selection operator, adaptive elastic, tree structured Bayesian model averaging, bootstrap aggregation, boosting, SCAD, MCP, and Dantzig selector, wherein execution of the ensemble of statistical models results in a predicted nicotine metabolic ratio for each study subject;
   d. comparing the predicted nicotine metabolic ratio calculated for each study subject based on the high dimensional data with the measured metabolic ratio for the respective study subject to determine an accuracy of each statistical learning model;
   e. executing the ensemble of statistical models on dimensional data of the new subject to predict potential nicotine metabolic ratios of the new subject based on the high dimensional data of the new subject,
   f. weighting each potential nicotine metabolic ratios of the new subject based on the accuracy of each statical model; and
   e. predicting a final nicotine metabolic ratio of the new subject.

2. The method of claim 1, wherein each of the statistical learning models in the ensemble apply a different penalized regression technique for regularization of the high dimensional data.

3. The method of claim 1, further comprising using a penalized regression technique to minimize a regression coefficient by minimizing a penalized residual sum of squares given by the equation:

$$\hat{\beta} = \underset{\beta}{\mathrm{argmin}} \sum_{i=1}^{N} \left( y_i - \beta_0 - \sum_{j=1}^{P_1} \beta_{1j} C_{ij} - \sum_{j=1}^{P_2} \beta_{2j} G_{ij} - \sum_{j=1}^{P_3} \beta_{3j} Z_{ij} \right)^2 + P(\beta, \lambda),$$

wherein i represents the study subject number, N represents a total number of study subjects, $y_i$ represents the nicotine metabolite ratio for the i-th subject, $P_1$ represents a number of cofounders, represents the $C_{ij}$ measured cofounder for study subject i, $P_2$ represents a number of genetic tactors, $G_{ij}$ represents the jth genetic factor for study subject i, P3 represents a number of derived variables, $Z_{ij}$ represents the jth derived variable for study subject i, $\lambda$ represents a collection of tuning parameters, $\beta$ denotes the collection of all regression coefficients, and $P(\beta,\lambda)$ is a penalty function.

4. The method of claim 1, wherein the ensemble of statistical learning models comprises a Bayesian linear regression technique.

5. The method of claim 4, wherein the ensemble of statistical learning models comprises derived variable.

6. The method of claim 5, wherein the wherein the derived variables are derived from the following system of equations:

$$Z_1 = \theta_{1,1} G_1 + \theta_{1,2} G_2 + (1 - \theta_{1,1} - \theta_{1,2}) G_1 G_2 \qquad \mathrm{a)}$$

$$Z_2 = \theta_{2,1} G_3 + \theta_{2,2} G_4 + (1 - \theta_{2,1} - \theta_{2,2}) G_3 G_4 \qquad \mathrm{b)}$$

$$Z_3 = \theta_{3,1} Z_1 + \theta_{3,2} Z_2 + (1 - \theta_{3,1} - \theta_{3,2}) Z_1 Z_2 \qquad \mathrm{c)}$$

wherein Z represents the derived variable, θ represents a weighting factor, and G represents genetic factors from the high dimensional data.

7. The method of claim 1, further comprising validating the final nicotine metabolic ratio.

8. The method of claim 7, further comprising cross validating the final nicotine metabolic ratio.

9. A method for developing a model for predicting a final biomarker for substance use disorders in a new subject, comprising:
   a. receiving high dimensional data, wherein receiving high dimensional data comprises collecting DNA samples from study subjects; genotyping the DNA samples collected; storing and processing data from the genotyped DNA samples collected on a server; and collecting individual characteristics of the study subjects on the server;
   b. measuring a known biomarker from each study subject and recording the measured biomarker for each study subject on the server;
   c. training a machine to learn to predict the final biomarker of the new subject by executing an ensemble of statistical learning models using the high dimensional data and known biomarkers of each study subject, wherein the statistical learning models are selected from the group consisting of least absolute shrinkage and selection operator, ridge estimator, elastic net, adaptive least absolute shrinkage and selection operator, adaptive elastic, tree structured Bayesian model averaging, bootstrap aggregation, boosting, SCAD, MCP, Dantzig selector, wherein execution of the ensemble of statistical models results in a predicted biomarker for each study subject;

d. comparing the predicted biomarker identified for each study subject based on the high dimensional data with the measured known biomarker for the respective study subject to determine an accuracy of each statistical learning model;

e. executing the ensemble of statistical models on high dimensional data of the new subject to predict potential biomarkers for the new subject based on the high dimensional data of the new subject, f. weighting each potential biomarker of the new subject based on the accuracy of each statical model; and e. predicting the final biomarker of the new subject.

10. The method of claim 9, further comprising minimizing a regression coefficient by minimizing a penalized residual sum of squares using the equation:

$$\hat{\beta} = \underset{\beta}{\operatorname{argmin}} \sum_{i=1}^{N} \left( y_i - \beta_0 - \sum_{j=1}^{P_1} \beta_{1j} C_{ij} - \sum_{j=1}^{P_2} \beta_{2j} G_{ij} - \sum_{j=1}^{P_3} \beta_{3j} Z_{ij} \right)^2 + P(\beta, \lambda),$$

wherein i represents the study subject number, N represents a total number of study subjects, $y_i$ represents the biomarker for the i-th subject, $P_1$ represents a number of cofounders, $C_{ij}$ represents the jth measured cofounder for study subject i, $P_2$ represents a number of genetic factors, $G_{ij}$ represents the jth genetic factor for study subject i, P3 represents a number of derived variables, $Z_{ij}$ represents the jth derived variable for study subject i, $\lambda$ represents a collection of tuning parameters, $\beta$ denotes the collection of all regression coefficients, and $P(\beta, \lambda)$ is a penalty function.

11. The method of claim 9, wherein each of the plurality of statistical learning models use Bayesian linear regression techniques.

12. The method of claim 11, wherein the ensemble of statistical learning models comprise a derived variable.

13. The method of claim 9, wherein the derived variables are derived from the following system of equations:

$$Z_1 = \theta_{1,1} G_1 + \theta_{1,2} G_2 + (1 - \theta_{1,1} - \theta_{1,2}) G_1 G_2 \qquad \text{a)}$$

$$Z_2 = \theta_{2,1} G_3 + \theta_{2,2} G_4 + (1 - \theta_{2,1} - \theta_{2,2}) G_3 G_4 \qquad \text{b)}$$

$$Z_3 = \theta_{3,1} Z_1 + \theta_{3,2} Z_2 + (1 - \theta_{3,1} - \theta_{3,2}) Z_1 Z_2 \qquad \text{c)}$$

wherein Z represents the derived variable, $\theta$ represents a weighting factor, and G represents genetic factors from the high dimensional data.

14. The method of claim 9, further comprising validating the final biomarker.

15. The method of claim 14, further comprising cross-validating the final biomarker using a k-fold cross validation technique.

16. The method of claim 9, wherein the final biomarker is used for diagnosing a disease or identifying a treatment protocol.

* * * * *